US007001374B2

(12) United States Patent
Peyman

(10) Patent No.: US 7,001,374 B2
(45) Date of Patent: Feb. 21, 2006

(54) ADJUSTABLE INLAY WITH MULTIZONE POLYMERIZATION

(75) Inventor: Gholam A. Peyman, New Orleans, LA (US)

(73) Assignee: Minu, L.L.C., Pittsboro, NC (US)

( * ) Notice: Subject to any disclaimer, the term of this patent is extended or adjusted under 35 U.S.C. 154(b) by 0 days.

(21) Appl. No.: 10/272,402

(22) Filed: Oct. 17, 2002

(65) Prior Publication Data

US 2004/0049174 A1    Mar. 11, 2004

Related U.S. Application Data

(63) Continuation-in-part of application No. 10/091,444, filed on Mar. 7, 2002, which is a continuation-in-part of application No. 09/532,516, filed on Mar. 21, 2000, now Pat. No. 6,436,092.

(51) Int. Cl.
*A61B 18/18* (2006.01)

(52) U.S. Cl. .......................... 606/5; 623/5.11; 351/159

(58) Field of Classification Search .................... 606/5; 623/5.11, 6.11, 6.56, 6.59, 6.6, 6.61, 6.62, 623/6.22, 6.32; 351/159, 162
See application file for complete search history.

(56) References Cited

U.S. PATENT DOCUMENTS

| | | | |
|---|---|---|---|
| 4,563,565 A | | 1/1986 | Kampfer et al. |
| 4,575,373 A | * | 3/1986 | Johnson ..................... 623/6.22 |
| 4,676,790 A | | 6/1987 | Kern |
| 4,718,418 A | | 1/1988 | L'Esperance, Jr. |
| 4,840,175 A | | 6/1989 | Peyman |
| 4,976,709 A | | 12/1990 | Sand |
| 4,994,058 A | | 2/1991 | Raven et al. |
| 5,120,121 A | * | 6/1992 | Rawlings et al. ........... 351/162 |
| 5,196,027 A | | 3/1993 | Thompson |
| 5,336,261 A | | 8/1994 | Barrett et al. |
| 5,647,865 A | | 7/1997 | Swinger |
| 5,722,971 A | | 3/1998 | Peyman |
| 5,824,086 A | | 10/1998 | Silvestrini |
| 5,919,185 A | | 7/1999 | Peyman |
| 6,102,946 A | | 8/2000 | Nigam |
| 6,361,560 B1 | | 3/2002 | Nigam |
| 6,413,276 B1 | * | 7/2002 | Werblin ..................... 623/6.32 |
| 6,450,642 B1 | | 9/2002 | Jethmalani et al. |
| 6,749,632 B1 | | 6/2004 | Sandstedt et al. |
| 6,813,097 B1 | | 11/2004 | Jethmalani et al. |
| 6,824,266 B1 | | 11/2004 | Jethmalani et al. |
| 6,851,804 B1 | | 2/2005 | Jethmalani et al. |
| 2002/0016629 A1 | | 2/2002 | Sandstedt et al. |
| 2002/0042004 A1 | | 4/2002 | Sandstedt et al. |
| 2002/0167735 A1 | | 11/2002 | Jethmalani et al. |
| 2002/0169505 A1 | | 11/2002 | Jethmalani et al. |
| 2003/0048411 A1 | | 3/2003 | Jethmalani et al. |
| 2003/0090013 A1 | | 5/2003 | Jethmalani et al. |
| 2003/0090624 A1 | | 5/2003 | Jethmalani et al. |

(Continued)

OTHER PUBLICATIONS

Karin R. Sletten, MD et al.; Experimental Science, "An In Vivo Model of Femtosecond Laser Intrastromal Refractive Surgery", Ophthalmic Surgery and Lasers, Nov./Dec. 1999, vol. 30, No. 9, pp. 742-749.

(Continued)

*Primary Examiner*—Julian W. Woo
(74) *Attorney, Agent, or Firm*—Bell, Boyd, & Lloyd LLC

(57) ABSTRACT

The present invention relates to an inlay for correcting refractive error in an eye. The inlay includes a first portion having a first volume that remains substantially constant when exposed to an energy, and a second portion having a second volume that is adapted to change when exposed to the energy. This inlay results in a device that can correct severe ametropic conditions, without ablating any portion of the inlay itself or the cornea.

37 Claims, 25 Drawing Sheets

U.S. PATENT DOCUMENTS

| | | |
|---|---|---|
| 2003/0093150 A1 | 5/2003 | Jethmalani et al. |
| 2003/0128336 A1 | 7/2003 | Jethmalani et al. |
| 2003/0151825 A1 | 8/2003 | Bielawski et al. |
| 2003/0151831 A1 | 8/2003 | Sandstedt et al. |
| 2003/0174375 A1 | 9/2003 | Jethmalani et al. |
| 2003/0176521 A1 | 9/2003 | Jethmalani et al. |

OTHER PUBLICATIONS

Griffith et al.; "Functional Human Corneal Equivalents Constructed from Cell Lines", Science, vol. 286, Dec. 10, 1999, pp. 2169-2172.

Yamauchi et al.; "Cultivation of fibroblast cells on keratin-coated substrata", Polymers for Tissue Engineering, pp. 329-340, VSP 1998.

Ijima et al.; "Formation of a spherical multicellular aggregate (spheroid) of animal cells in the pores of polyurethane foam as a cell culture substratum and its application to a hybrid artificial liver", Polymers for Tissue Engineering, pp. 273-286, VSP 1998.

Cao et al.; "Comparative study of the use of poly(glycolic acid), calcium alginate and pluronics in the engineeering of autologous porcine cartilage", Polymers for Tissue Engineering, pp. 315-327, VSP 1998.

Jose I. Barraquer, M.D., "Keratomileusis and keratophakia in the surgical correction of aphakia", pp. 270-289, published before Mar. 21, 2000.

* cited by examiner

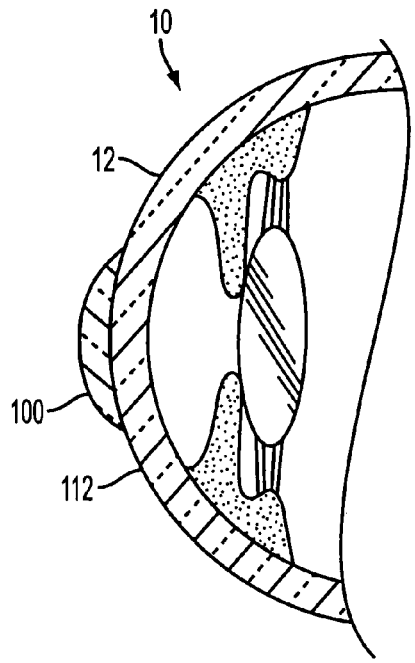
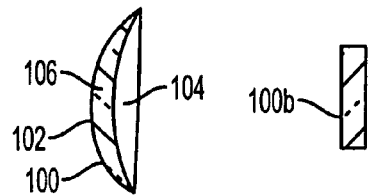
FIG. 36a  FIG. 36b
FIG. 35
  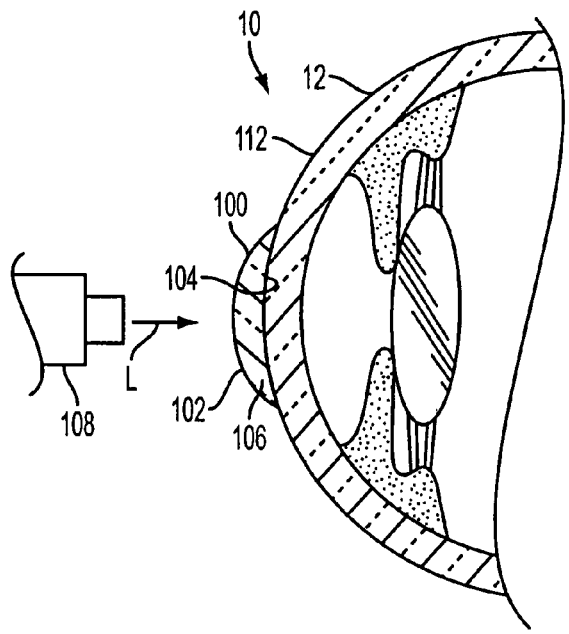
FIG. 36c  FIG. 36d
FIG. 37

ADJUSTABLE INLAY WITH MULTIZONE POLYMERIZATION

This application is a continuation-in-part of application Ser. No. 10/091,444, filed Mar. 7, 2002, and titled "Adjustable Universal Implant Blank for Modifying Corneal Curvature and Methods of Modifying Corneal Curvature Therewith", which is a continuation-in-part of application Ser. No. 09/532,516, filed Mar. 21, 2000, and titled "An Adjustable Universal Implant Blank for Modifying Corneal Curvature and Methods of Modifying Corneal Curvature Therewith", now U.S. Pat. No. 6,436,092, the entire contents of both of which are herein incorporated by reference.

CROSS-REFERENCE TO RELATED PATENTS AND APPLICATIONS

Related subject matter is disclosed in U.S. Pat. Nos. 5,919,185, 5,722,971 and 4,840,175, in a copending application entitled "A Universal Implant Blank for Modifying Corneal Curvature and Methods of Modifying Corneal Curvature Therewith", Ser. No. 09/260,591, filed Mar. 2, 1999; and in a copending application entitled "Instrastromal Corneal Modification", Ser. No. 09/260,571, filed Mar. 2, 1999. The entire contents of each of the above-referenced patent applications and patents are incorporated herein by reference.

BACKGROUND OF THE INVENTION

1. Field of the Invention

The present invention relates to an adjustable inlay, which is used to modify the curvature of a live cornea when implanted therein. The inlay includes a first zone or portion and a second zone or portion. The first zone is formed from synthetic or organic material which can cause the volume of the inlay to increase or decrease in volume when that area is irradiated with energy such as light of a particular wavelength, microwaves, or thermal energy. The second zone preferably has a fixed volume, so that when irradiated by an energy such as light of a particular wavelength, microwaves, or thermal energy the volume will remain substantially constant.

2. Description of the Related Art

A normal emetropic eye includes a cornea, lens and retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused in back of the retina.

An eye suffering from astigmatism has a defect in the lens or shape of the cornea. Therefore, an astigmatic eye is incapable of sharply focusing images on the retina.

Optical methods are known which involve the placement of lenses in front of the eye, for example, in the form of glasses or contact lenses, to correct vision disorders. A common method of correcting myopia is to place a "minus" or concave lens in front of the eye in order to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. The concave, convex or other shaped lenses are typically configured in the form of glasses or contact lenses.

Although these optical methods can be used to correct vision in eyes suffering from low myopia up to 6 diopters, or in eyes suffering from hypermetropic, hyperopic or astigmatic conditions which are not very severe, that method is ineffective in correcting vision in eyes suffering from sever forms of ametropia. For example, known optical methods are typically ineffective in correcting high myopia of 6 diopters or greater, and are also ineffective in correcting severe astigmatism and severe forms of hypermetropia or hyperopia.

However, surgical techniques exist for correcting these more severe forms of ametropia to a certain degree. For example, in a technique known as myopic keratomileusis, a microkeratome is used to cut away a portion of the front of the live cornea from the main section of the live cornea. The cut portion of the cornea is frozen and placed in a cryolathe where it is cut and reshaped. Altering the shape of the cut portion of the cornea changes the refractive power of this cut portion, which thus affects the location at which light entering the cut portion of the cornea is focused. The reshaped cut portion of the cornea is then reattached to the main portion of the live cornea. Hence, it is intended that the reshaped cornea will change the position at which the light entering the eye through the cut portion is focused, so that hopefully the light is focused on the retina, thus remedying the ametropic condition.

The myopic keratomileusis technique is known to be effective in curing myopic conditions within a range of 6 to 18 diopters. However, the technique is impractical because it employs very complicated and time consuming freezing, cutting and thawing processes. Furthermore, the technique is ineffective in correcting myopic conditions greater than 18 diopters.

Keratophakia is another known surgical technique for correcting sever ametropic conditions of the eye by altering the shape of the eye's cornea. In this technique an artificial organic or synthetic lens is implanted inside the cornea to thereby alter the shape of the cornea and thus change its refractive power. Accordingly, as with the myopic keratomileusis technique, it is desirable that the shape of the cornea be altered to a degree allowing light entering the eye to be focused correctly on the retina.

However, the keratophakia technique is impractical, complicated, and expensive because it requires manufacturing or cutting a special lens prior to its insertion into the cornea. Hence, a surgeon is required to either maintain an assortment of many differently shaped lenses, or alternatively, must have access to expensive equipment, such as a cyrolathe, which can be used to cut the lens prior to insertion into the cornea. Examples of known techniques for modifying corneal curvature, such as those discussed above, are described in U.S. Pat. No. 4,994,058 to Raven et al., U.S. Pat. No. 4,718,418 to L'Esperance, U.S. Pat. No. 5,336,261 to Barrett et al., and a publication by Jose I. Barraquer, M. D. entitled "Keratomileusis and Keratophakia in the Surgical Correction of Aphakia". The entire contents of each of these patents are incorporated herein by reference.

Surgical techniques involving the use of ultraviolet and shorter wavelength lasers to modify the shape of the cornea also are known. For example, excimer lasers, such as those described in U.S. Pat. No. 4,840,175 to Peyman, referenced above, which emit pulsed ultraviolet radiation, can be used to decompose or photoablate tissue in the live cornea so as to reshape the cornea.

Specifically, a laser surgical technique known as laser in situ keratomycosis (LASIK) has been previously developed by the present inventor. In this technique, a portion of the front of a live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150–180 microns deep. The cut portion is then reattached over the ablated portion of the cornea and assumes a shape conforming to that of the ablated portion.

However, because only a certain amount of cornea can be ablated without the remaining cornea becoming unstable or experiencing outbulging (eklasia), this technique is not especially effective in correcting very high myopia. That is, a typical live cornea is on average about 500 microns thick. The laser ablation technique requires that at least about 200 microns of the corneal stroma remain after the ablation is completed so that instability and outbulging does not occur. Hence, this procedure typically cannot be effectively used to correct high myopia of greater than 15 diopters because in order to reshape the cornea to the degree necessary to alter its refractive power so as to sufficiently correct the focusing of the eye, too much of the cornea would need to be ablated.

Accordingly, as described in U.S. Pat. No. 5,919,185 cited above, another technique has been developed by the present inventor which involves placing a universally sized blank made of organic or synthetic material on an exposed inner surface of a live cornea, and ablating the blank with a laser beam to alter the blank to a particular shape. Specifically, a flap-like portion of the live cornea is removed to expose an inner surface of the cornea, and the blank is positioned on the exposed inner surface of the eye. A laser beam is directed onto certain portions of the blank that are selected based on the type of ametropic condition (i.e., myopia, hyperopia or astigmatism) of the eye needing correction, so that the laser beam ablates those portions and thus reshapes the blank. The laser beam can also be directed onto certain portions of the laser surface of the cornea to ablate those surfaces of the cornea. The flap-like portion of the cornea is repositioned over the remaining portion of the blank, so that the remaining portion of the blank influences the shape of the reattached flap-like portion of the cornea and thus modifies the curvature of the cornea.

This technique is effective in modifying the curvature of the cornea to correct the types of severe vision disorders described above. Also, after the initial procedure has been performed, it is at times necessary to further modify the size and shape of the implanted blank to make fine adjustments to its refractive power, and thus further improve the patient's vision. In this event, it may be necessary to reopen the flap in the cornea, and either further ablate the blank on the exposed corneal surface, or replace the blank with another blank having a size and shape more suitable to correct the vision disorder. However, this additional surgery can create the risk of damage to the patient's eye, and cause further patient discomfort.

A need therefore exists for improved methods for further modifying an implanted inlay or contact lens to better correct very severe ametropic conditions.

SUMMARY OF THE INVENTION

An object of the present invention is to provide a system and method for adjusting, without ablation, the size and shape of a blank that has been implanted into a live cornea to modify corneal curvature to thus correct severe ametropic conditions.

Another object of the invention is to provide a blank that can be implanted into a live cornea to modify corneal curvature to thus correct severe ametropic conditions, and which is modifiable without ablation.

A further object of the invention is to provide a blank including a material that increases the volume of the blank in response to energy, and which further includes a material that shrinks or decreases the volume of the blank in response to energy, without ablating the blank.

Still a further object of the present invention is to provide an ablatable implant that can be implanted between layers of the cornea to improve vision in the eye.

Yet a further object of the present invention is to provide a method of correcting refractive error in the eye by ablating an implant on the surface of the cornea and subsequently positioning the implant under a flap formed in the corneal surface of the eye.

Another object of the present invention is to provide a system and method for adjusting, without ablation, the size and shape of an inlay that has been placed adjacent a surface of the cornea.

Another object of the present invention is to provide a system and method for adjusting, without ablation, the size and shape of an inlay that has been implanted into a live cornea to modify corneal curvature to thus correct severe ametropic conditions.

A further object of the present invention is to provide an inlay that can be implanted into a live cornea to modify corneal curvature to thus correct severe ametropic conditions, and which is modifiable without ablation.

Still a further object of the invention is to provide an inlay for correcting the refractive error in the eye and includes a material that increases the volume of the inlay in response to energy, and which further includes a material that shrinks or decreases the volume of the inlay in response to energy, without ablating the inlay.

Yet a further object of the present invention is to provide an inlay for correcting the refractive error in the eye that has a first portion with a first volume that remains substantially constant when exposed to an energy, and a second portion with a second volume that is adapted to change when exposed to the same energy.

Still yet another object of the present invention is to provide a method of correcting refractive error in the eye by ablating an implant on the surface of the cornea and subsequently positioning the implant under a flap formed in the corneal surface of the eye.

The foregoing objects are basically attained by an inlay for correcting refractive error in an eye, including a first portion that has a first volume that remains substantially constant when exposed to an energy, and a second portion that has a second volume that is adapted to change when exposed to the energy.

The foregoing objects are further attained by an inlay for correcting refractive error in an eye, including a first portion formed from a first material, and a second portion formed from a second material. At least a portion of the second material is adapted to increase in volume, when exposed to a first energy, or decrease in volume, when exposed to a second energy, while the volume of the first material remains substantially unchanged.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

These and other objects and advantages of the invention will become more apparent and more readily appreciated from the following detailed description of the presently preferred exemplary embodiments of the invention taken in conjunction with the accompanying drawings, of which:

FIG. 35 is an elevational side view in section of an eye with an implant on the surface thereof;

FIGS. 36a–36d are elevational side views in section of the various types of lenses that can be used in the procedure shown in FIGS. 35 and 37–43;

FIG. 37 is an elevational side view in section of the implant shown in FIG. 35 being ablation by a laser;

DETAILED DESCRIPTION OF THE INVENTION

Figure 1:
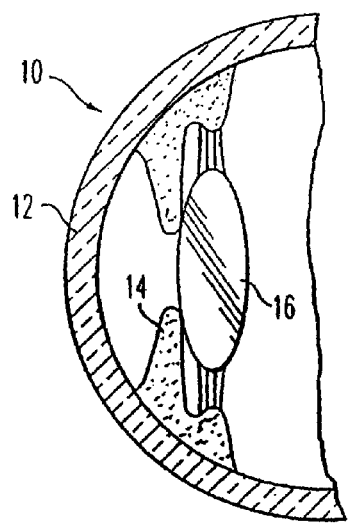
FIG. 1 is a side elevational view in section taken through the center of an eye showing the cornea, pupil and lens.

FIG. 1 is a side elevational view in section taken through the center of an eye 10 which includes a cornea 12, a pupil 14 and a lens 16. If the cornea 12 and lens 16 do not cooperatively focus light correctly on the retina (not shown) of the eye to thus provide adequate vision, the curvature of the cornea can be modified to correct the refractive power of the cornea and thus correct the manner in which the light is focused with respect to the retina.

Figure 2:
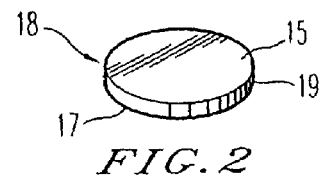
FIG. 2 is a perspective view of an embodiment of a universal blank according to the present invention.
Figure 3:
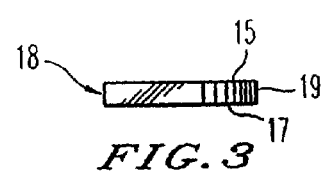
FIG. 3 is a front elevational view of the embodiment shown in FIG. 2.
Figure 4:
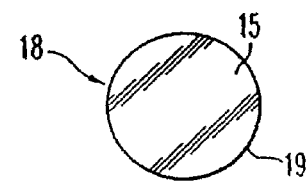
FIG. 4 is a top elevational view of the embodiment shown in FIG. 2.

A universal blank 18 according to an embodiment of the present invention is illustrated in FIGS. 2–4. As shown, the universal blank according to this embodiment is disk-shaped and has a uniform or substantially uniform thickness throughout, as illustrated specifically in FIG. 3. Specifically, the blank 18 has a first planar or substantially planar surface 15, a second planar or substantially planar surface 17, and a periphery 19. The surfaces 15 and 17 are arranged parallel or substantially parallel to each other with the periphery 19 being perpendicular or substantially perpendicular to one or both surfaces 15 and 17. Of course, the surfaces 15 and 17 and the periphery 19 need not be uniform but could have recesses, projections, raised portions, or any variation in shape and texture. Preferably, the universal blank 18 has a diameter of about 1 mm to about 10 mm and a thickness of between about 20 to about 500 microns, or up to several millimeters. Of course, the diameter and thickness of the disk-shaped universal blank 18 can be of any practical size as would be appreciated by one skilled in the art. Furthermore, the universal blank need not be disk-shaped although it is preferred as shown in the embodiment of FIGS. 2–4, but can be frusto-conical, oval, square, rectangle, or any practical shape as would be readily appreciated by one skilled in the art.

The blank 18 is preferably made of synthetic material, organic material, or a combination of both synthetic and organic material, that permits all or substantially all light having a wavelength in the visible spectrum to pass through, but absorbs all or substantially all light having a wavelength in a laser light spectrum. For example, the blank 18 can be made of collagen, copolymer collagen, polyethylene oxide, polypropylene, polyproledine or hydrogel, or cross-linked organic material such as collagen, hyaluronic acid, mucopolysacoharide or glycoprotein, to name a few. The blank 18 is porous to allow oxygen and nutrients to pass therethrough. Also, the blank 18 can be made from a donor cornea of a human eye, or can be taken from a cultured cornea. However, the blank 18 is not limited to those materials, and can be made of any suitable material, such as those disclosed in U.S. Pat. No. 4,994,058 to Raven et al., U.S. Pat. No. 4,718,418 to L'Esperance, U.S. Pat. No. 5,336,261 to Barrett et al., U.S. Pat. No. 4,840,175 to Peyman, and a publication by Jose I. Barraquer, M. D. entitled "Keratomileusis and Keratophakia in the Surgical Correction of Aphakia", the disclosures of which are hereby incorporated by reference herein.

The blank 18 can also be made of a hybrid material, which can be a combination of organic material and one or more polymers, such as those described above. The blank 18 can further be made of or include a tissue matrix comprising a collagen-chondroitin sulfate substrate, which is cross-linked with 0.02% to 0.04% glutaraldehyde and then treated with glylcine to remove unbound glutaraldehyde, as described in a publication by May Griffith et al. entitled "Functional Human Corneal Equivalents Constructed from Cell Lines", *Science*, Vol. 286, Dec. 10, 1999. The blank 18 can further include fibroblast cells on keratin-coated substrata, as described in an article by Kiyoshi Yamauchi et al. entitled "Cultivation of Fibroblast Cells on Keratin-Coated Substrata", *Polymers for Tissue Engineering,* 1998, pp. 329–340, or a spherical multicelluslar aggregate of animal cells in the pores of polyurethane foam as described in an article by Hiroyuki Ijima et al. entitled "Formation of a Spherical Multicellular Aggregate (Spheroid) of Animal Cells in the Pores of Polyurethane Foam as a Cell Culture Substream and its Application to a Hybrid Artificial Liver", *Polymers for Tissue Engineering,* 1998, pp. 273–286. Also, the blank 18 can include polyglycolic acid, calcium alginate and pluronics in autologous porcine cartilage as described in an article by Yilin Cao et al. entitled "Comparative Study of the Use of Poly(glycolic acid), Calcium Alginate and Pluronics in the Engineering of Autologous Porcine Cartilage", *Polymers for Tissue Engineering,* 1998, pp. 315–327.

Furthermore, for reasons discussed in detail below, the blank 18 can include a silicone polymer which includes loose monomers that are responsive to light within a certain wavelength range, such as the short ultraviolet wavelength range or the blue light wavelength range. In response to the light, the monomers become aggravated, and cross-linking occurs which increases the volume of the area of the blank 18 being irradiated with the light.

The blank 18 can also include a polymer comprising a polycarbonate or acrylic material containing a dye or dyes manufactured, for example, by Centex Company. The dye or dyes absorb light within a certain wavelength range, such as the infrared wavelength range, which causes slight melting or softening of the material. This melting or softening results in a decrease or flattening of the irradiated area of the blank 18, and thus reduces the volume of that area for purposes discussed in more detail below.

Figure 5:
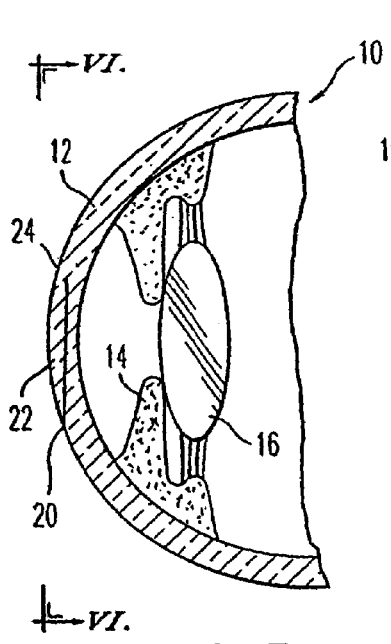
FIG. 5 is a side elevational view in section taken through the center of an eye showing formation of a flap-like structure at the front of the cornea.

The blank 18 is configured to be placed directly on an exposed inner surface of the cornea of the eye. In order to expose this inner surface of the cornea of the eye, a thin layer of the live cornea must be removed. To remove the layer of the cornea, a procedure is performed in which, for example, an incision 20 is made in the front portion of the cornea, as shown in FIG. 5. This incision 20 is made so as to separate thin layer 22 of the cornea from the remaining portion of the cornea 12. The incision can be made with a scalpel, keratome, excimer laser, or any type of surgical cutting instrument known to one skilled in the art. The layer 22 can also be separated from the surface of the live cornea by any other method which may not involve making an actual incision in the cornea as may be appreciated by one skilled in the art.

Figure 6:
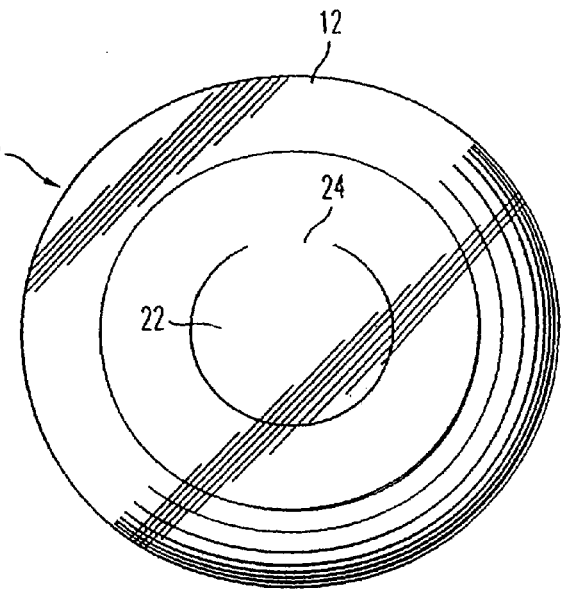
FIG. 6 is a front elevational view of the cornea and flap-like structure as taken along lines VI—VI in FIG. 5.
Figure 7:
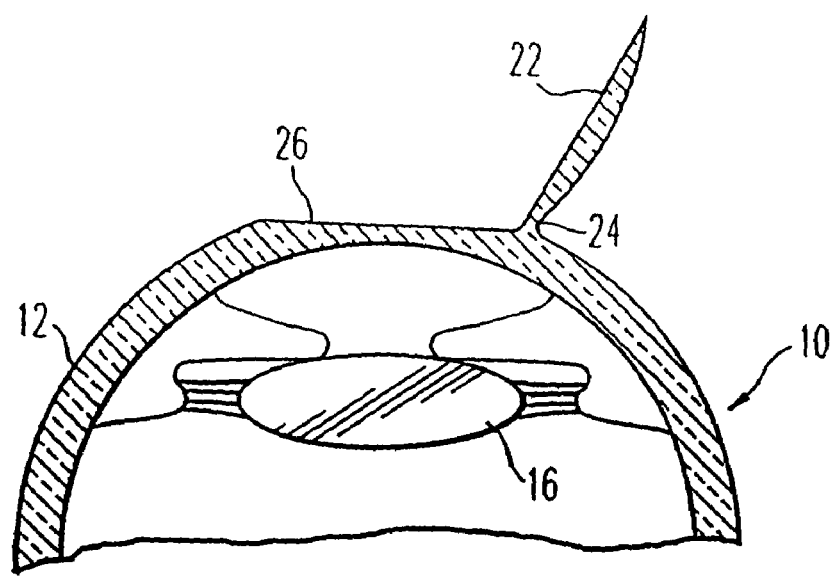
FIG. 7 is a side elevational view in section taken through the center of an eye and showing the flap-like section positioned to expose an inner surface of the cornea.

The layer 22 of the cornea can be completely removed from the remaining portion of the cornea 12. However, as shown in FIGS. 5 and 6, it is preferable that the layer 22 of the cornea remain attached to the main portion of the live cornea 12 by an attaching or hinging portion 24 Accordingly, as shown in FIG. 7, the layer 22 of the cornea is formed as a flap-like layer that is pivotally moveable about the attaching portion 24 to expose an inner surface 26 of the cornea. The layer 22 typically can be of any practical thickness, for example, 160 microns, and can have a uniform thickness throughout or a varying thickness.

The universal blank 18 is then used to modify the curvature of the cornea in the following manner.

Figure 8:
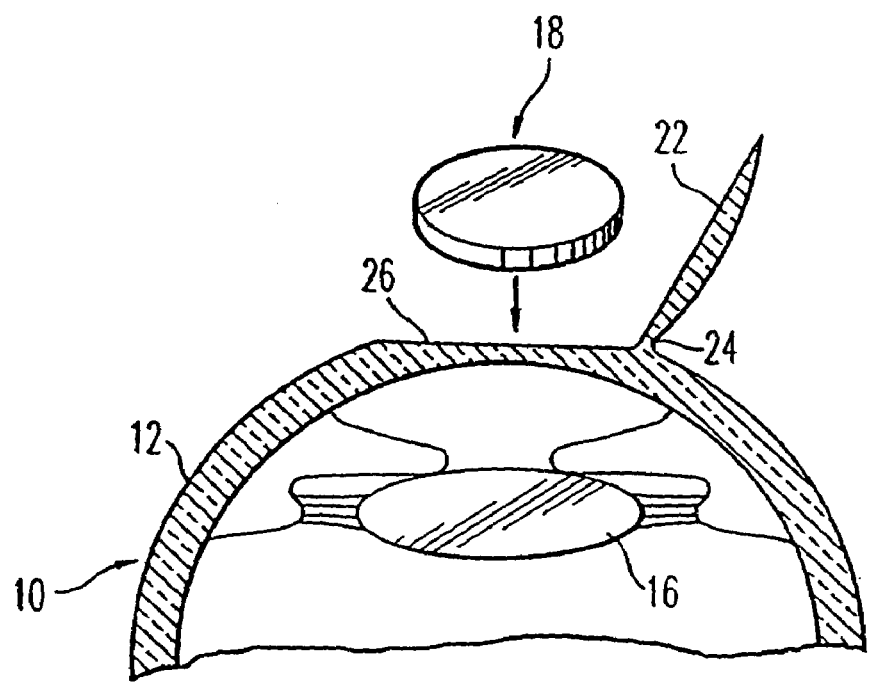
FIG. 8 is an enlarged side elevational view in section taken through the center of an eye and showing placement of the embodiment of the universal blank shown in FIG. 2 on the exposed surface of the cornea.
Figure 9:
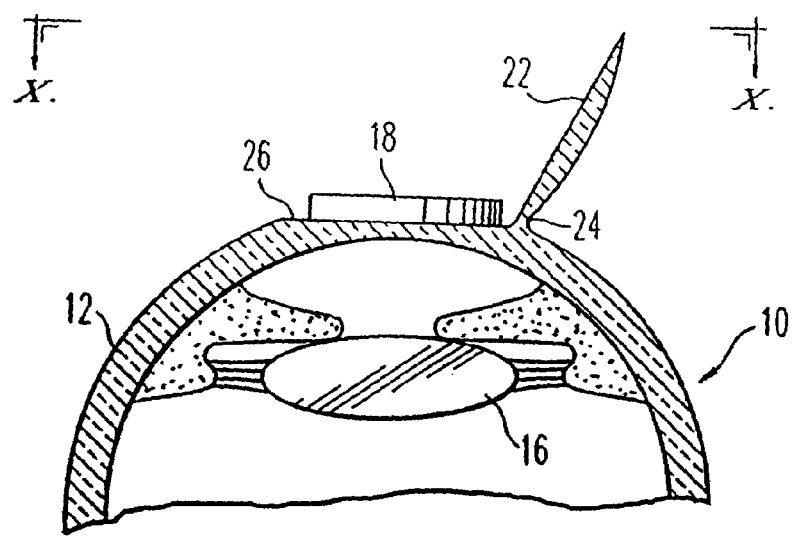
FIG. 9 is an enlarged side elevational view in section taken through the center of an eye and illustrating the universal blank shown in FIG. 2 positioned on the exposed surface of the cornea.
Figure 10:
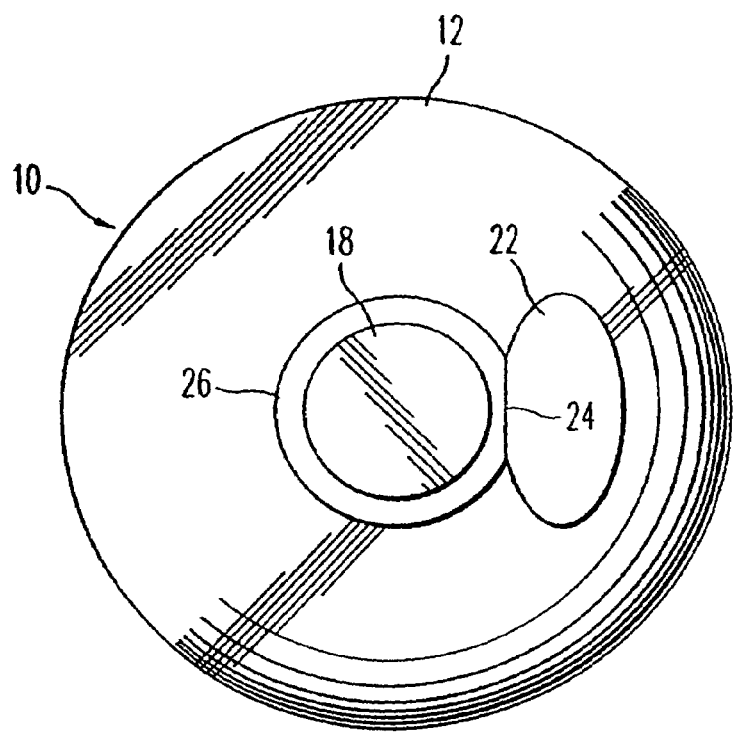
FIG. 10 is a front elevational view of the cornea with the universal blank present on the exposed surface thereof as taken along lines X—X in FIG. 9.
Figure 11:
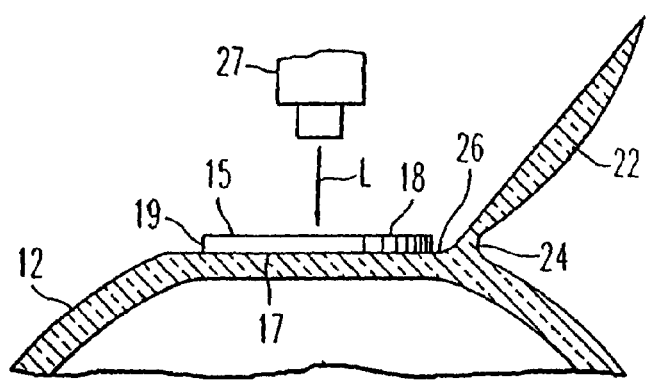
FIG. 11 is an enlarged side elevational view in section taken through the center of the eye showing the cornea and the irradiation of a laser beam on the universal blank positioned on the exposed surface of the cornea.

As shown in FIGS. 8 and 9, the flap-like layer 22 is positioned so as to expose the inner surface 26 of the cornea. The blank 18 is then positioned on the exposed surface of the cornea at a position deemed suitable by the person performing the cornea modifying technique. Typically, as shown in FIG. 10, the blank 18 is positioned centrally or substantially centrally on the exposed surface 26 with the central longitudinal axis of the blank substantially coincident with the central optical axis of the eye. Of course, the blank 18 need not be positioned centrally on the exposed surface 26 as shown, but rather, its central longitudinal axis can be offset from the central optical axis of the eye.

Once positioned on the exposed surface 26 of the cornea 12, the shape of the universal blank can be modified sufficiently to influence the shape of the flap-like layer 22 and to thus change the refractive power of the flap-like layer sufficiently to correct the abnormality of the eye 10. Generally, every 10 micron change in curvature of the cornea will change the refractive power of the cornea by 1 diopter.

For example, as shown in FIGS. 11–14, a laser beam L is directed to the first upper surface 15 of the blank 18 that is opposite to the second lower surface 17 of the blank 18 that is supported on the exposed surface 26 of the cornea 12. The laser beam L can be emitted from any type of laser 27 typically used in eye surgery methods, such as an excimer laser 27 or the like as described in U.S. Pat. No. 4,840,175.

Figure 12:
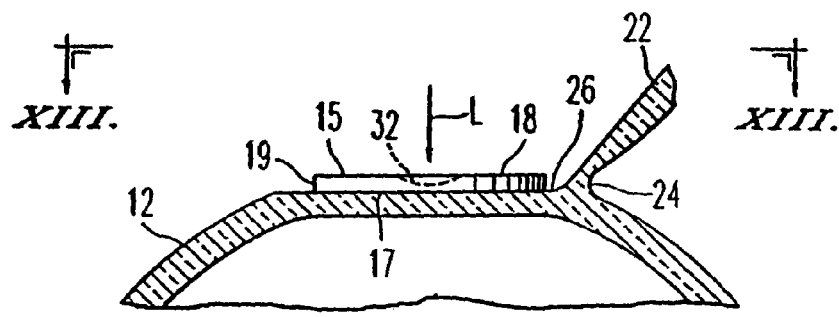
FIG. 12 illustrates ablation of the center of the universal blank by the laser beam.

As shown in FIG. 12, the laser beam L will begin to ablate or erode an area 32 of the blank 18 to which the laser beam is directed. Alternatively, the blank 18 can be made to the appropriate shape prior to placing it on the exposed surface of the cornea. Again, the area of the blank 18 to which the laser beam L is directed and which is ablated is selected to remedy a specific type of abnormality from which the eye is suffering.

Figure 13:
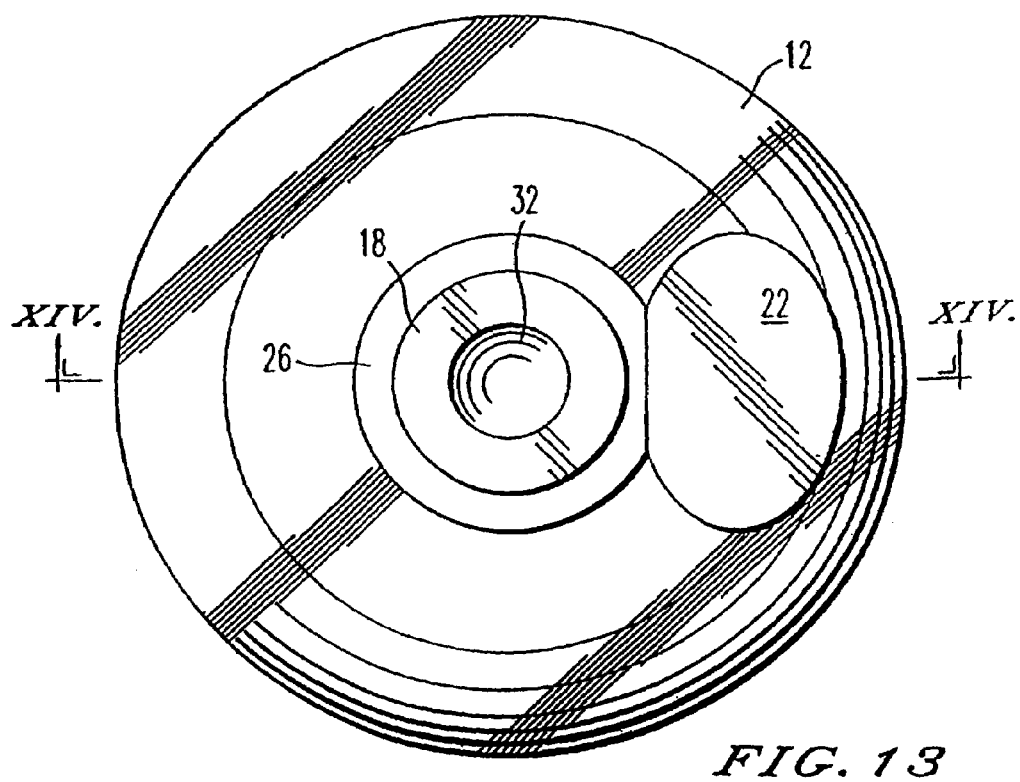
FIG. 13 is a reduced front elevational view of the ablated universal blank taken along lines XIII—XIII in FIG. 12.

For example, if the blank is being used to correct a myopic condition, the laser beam L will be directed toward a central area 32 of the blank 18 so as to ablate that central area 32. As shown in FIG. 13, for example, the blank 18 is, disk-shaped, and the area 32 that is ablated is circular in top plan view and is at least initially in the form of a substantially hemispheric recess. Of course, the shape of the ablated area can be any desired shape necessary to effect correction of the particular abnormality of the eye.

As stated previously, the blank 18 is made of a material that will absorb all or substantially all light having a wavelength within a laser light spectrum. Therefore, when the laser beam L is irradiated onto the blank 18, none or substantially none of the laser beam will pass through the blank 18 to ablate any portion of the cornea 12. However, as also previously stated, the material of the blank 18 will allow all or substantially all light having a wavelength within the visible light spectrum to pass therethrough.

Figure 14:
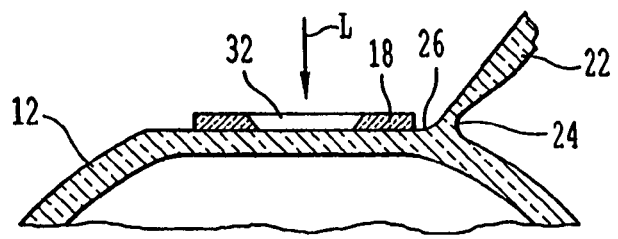
FIG. 14 is an enlarged cross-sectional view of the blank and cornea as taken along lines XIV—XIV in FIG. 13.

Hence, as shown in FIG. 14, the laser beam L can be directed to the blank 18 until the ablated central area 32 becomes a hole with a frustoconical wall which passes entirely through the blank 18 to expose a portion 34 of the surface 26 of the cornea 12. Of course, the hole can have a cylindrically or substantially cylindrically shaped wall, or any other shape as would be formed by the laser beam L. As shown in FIG. 14, none or essentially none of the surface 26 of the cornea has been ablated by the laser beam.

Figure 15:
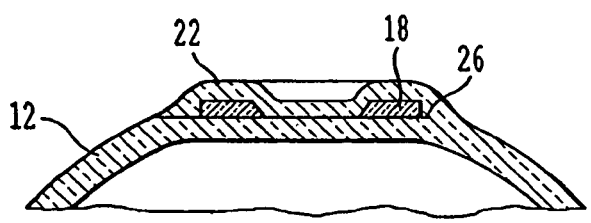
FIG. 15 is a side elevational view in section taken through the center of the eye showing the cornea and the flap-like portion reattached over the exposed surface of the cornea and the remaining portion of the ablated universal blank shown in FIG. 14.

After the laser ablation process has been completed, the flap-like layer 22 of the cornea is repositioned over the remaining portion of the blank 18 and the surface 26 of the cornea 12 as shown, for example, in FIG. 15. As illustrated, the shape of the remaining portion of the blank 18 will influence the shape of the flap-like layer 22 when the flap-like layer is repositioned over the remaining portion of the blank 18 and surface 26 of the cornea 12. Hence, the refractive power of this flap-like layer 22 will be changed due to this change in shape. The flap-like layer 22 can be reattached to the cornea 12 by any known techniques such as suturing, tissue adhesive, or the like.

Because the material of the blank 18 is transparent or essentially transparent to light having a wavelength within the visible light spectrum, visible light will pass through the remaining portion to the blank 18 and enter the eye 12. However, because the reshaped flap-like layer 22 has a different refractive power, the flap-like layer 22 will refract the light passing therethrough differently than prior to the reshaping. Therefore, in cooperation with the lens 16 (see FIG. 1), this reshaped layer 22 will focus the light in the appropriate manner on the retina, thus correcting the ametropic condition of the eye.

It is further noted that the laser 27 can be used to reduce the overall thickness of the blank 18 prior to shaping the blank. For instance, the blank 18 can initially be about 500 microns thick for ease of handling. Then, once the blank 18 is positioned on the exposed inner surface of the cornea in the manner described above, the inner beam L can be directed to the upper surface 15 of the blank so as to reduce the overall thickness of the blank 18 as desired. Hence, a 500 micron thick blank can be reduced, for example, to about 100 microns or any suitable thickness by the laser beam L before the laser beam L is used to sculpt the blank 18 to a particular shape as shown, for example, in FIGS. 11–15.

Additionally, based on the severity of the abnormality from which the eye is suffering, it may be determined that the surface of the cornea must be reshaped more extensively, or in other manners, which are described in U.S. Pat. No. 5,919,185 referenced above.

Once the universal blank 18 has been implanted and ablated as discussed above, and the layer 22 has been replaced, the patient's vision can then be monitored as the cornea 12 heals. If it is then determined that further adjustment should be made to curvature of the cornea 12, the size and shape of the blank 18 can be adjusted without surgically separating the layer 22 from the remainder of the cornea 12. That is, as discussed above, the blank 18 can include certain monomers which, when irradiated with light within a certain wavelength range (e.g., blue or ultraviolet light), become agitated and cross-link, which causes the blank 18 to increase in size at the area of the irradiation. Furthermore, the blank 18 can include a material comprising dyes as discussed above which will absorb laser light (continuous or pulsed) of a particular wavelength (e.g., infrared light) that is irradiated onto an area of the blank 18 to cause melting of the blank 18 in that irradiated area, without ablating the irradiated area. It is noted that when the pulsed laser light is focused properly to a location within the blank, it can disrupt and thus shrink or melt the blank without the need of an absorbent dye. An example of such a laser is a laser which emits nanosecond pulses, pico-second pulses or femtosecond pulses of laser light. Furthermore, laser light having a wavelength that is absorbed by water, or other types of energy such as microwave radiation, radio frequency radiation, or thermal energy, can be used to cause shrinkage in the blank without ablating the blank 18 and without lifting the layer 22. In any of the above methods, the additional shaping of the blank 18 is performed substantially without causing damage to the layer 22.

Figure 16:
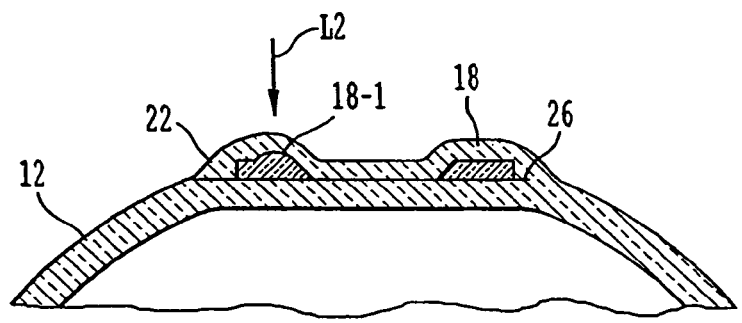
FIG. 16 is a side elevational view in section taken through the center of the eye showing the cornea and the flap-like portion reattached over the exposed surface of the cornea and the remaining portion of the ablated universal blank shown in FIG. 14, with the remaining portion of the blank further being irradiated with light of a particular wavelength to increase the volume of the irradiated area.

As shown in FIG. 16, an area 18-1 is irradiated by laser light which passes through the layer 22. The laser light L2 has a wavelength, such as long ultraviolet wavelength or light within the blue light spectrum, to aggravate the monomers, which causes a cross-linking effect that increases the volume of the blank 18 in the area 18-1 being irradiated. Hence, as the thickness of the blank 18 increases in the area 18-1, this increase thickness changes the curvature of the flap as shown, thus changing the refractive power of the cornea to a degree necessary to correct the remainder of the vision disorder that was not corrected by the ablated blank 18.

Figure 17:
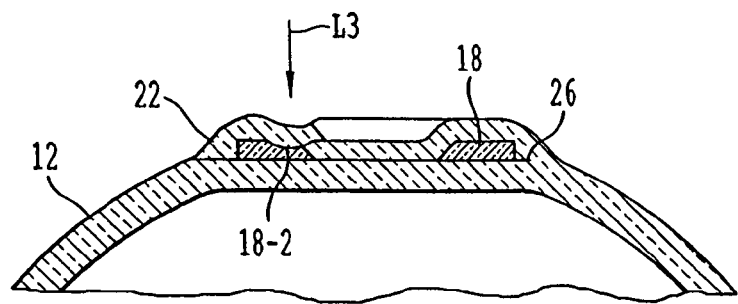
FIG. 17 is a side elevational view in section taken through the center of the eye showing the cornea and the flap-like portion reattached over the exposed surface of the cornea and the remaining portion of the ablated universal blank shown in FIG. 14, with the remaining portion of the blank further being irradiated with energy to decrease the volume of the irradiated area.

Alternatively, as shown in FIG. 17, an area 18-2 of the blank 18 is irradiated with energy L3, such as infrared light, laser light, microwave energy, radio frequency energy, or heat applied by a probe (not shown), to cause the area 18-2 of the blank to shrink or, in other words, reduce in volume. This shrinkage occurs with or without further ablation of the blank 18 and without damage to the layer 22 or other portion of the cornea 12. Accordingly, the shrinkage causes a change in the shape of the layer 22 over the area 18-2, and thus changes the refractive power of the layer 22 to further correct for the remaining vision disorder that was not fully corrected by the ablated blank 18.

Figure 18:
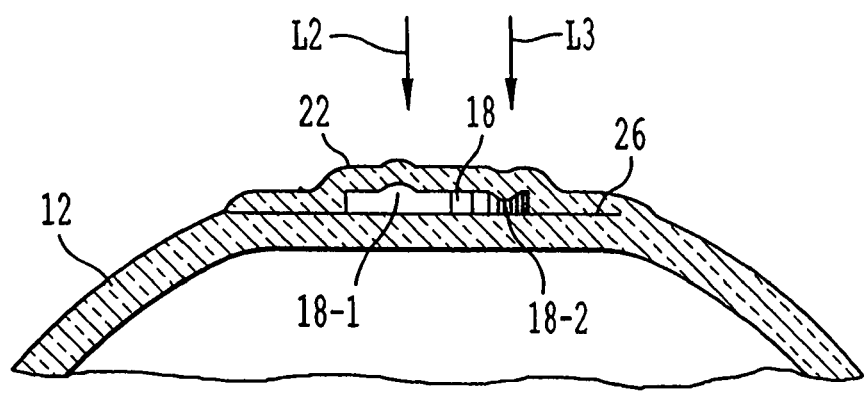
FIG. 18 is a side elevational view in section taken through the center of the eye showing the cornea and the flap-like portion reattached over the exposed surface of the cornea and an unablated universal blank, with the blank further being irradiated with light and energy and respective first and second areas to increase and decrease the volumes, respectively, of the irradiated areas.

It is further noted that as shown in FIG. 18, the blank 18 can be implanted in the cornea under the layer 22 without ablation. Then, in a manner similar to that described above, the particular light or energy can be applied to the areas of the blank, for example, areas 18-1 and 18-2, to create an increase or decrease in volume, as appropriate. This increase or decrease in volume of the areas 18-1 and 18-2 of blank 18 changes the shape of the layer 22, and thus changes the overall refractive power of the layer 22 in a manner similar to that discussed above with regard to the ablated blank 18. Accordingly, this change of shape corrects the vision disorder, as necessary, without the need for ablating the blank 18.

Figure 19A:
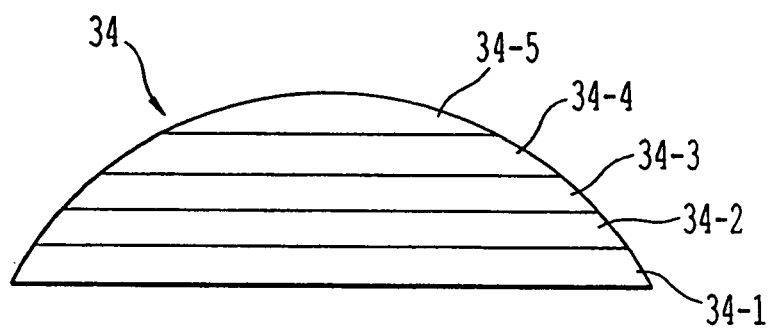
FIGS. 19A and 19B are side views of multi-layer blanks according to other embodiments of the present invention.
Figure 19B:
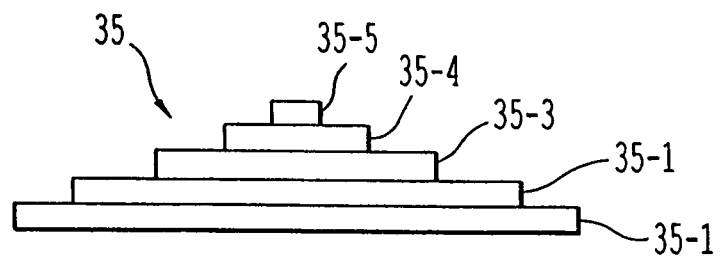
Figure 20:
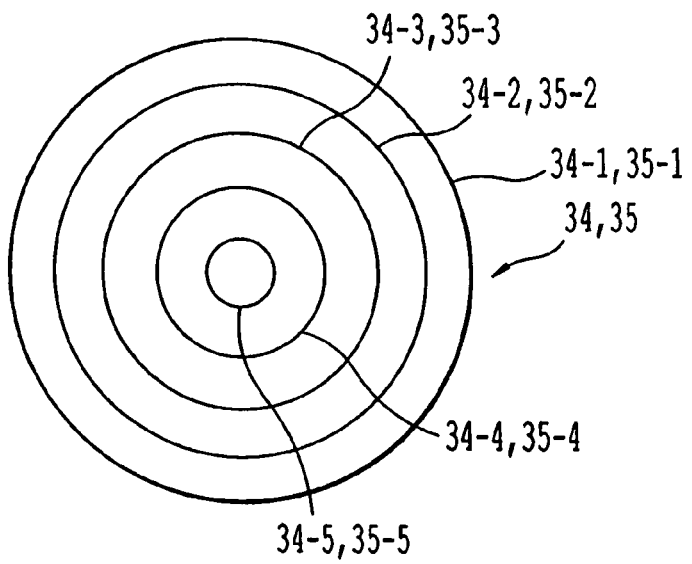
FIG. 20 is a top view of the multi-layer blank shown in FIG. 19A or 19B.
Figure 21:
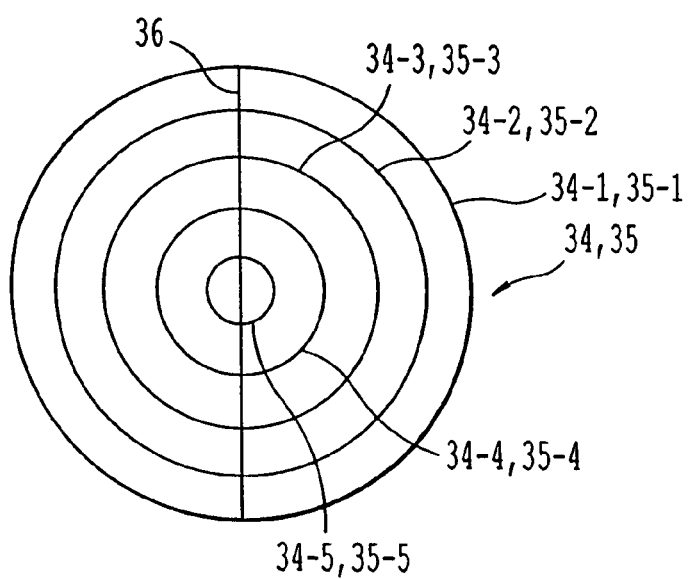
FIG. 21 is a top view of the multi-layer blank shown in FIG. 20 divided into two sections.
Figure 22:
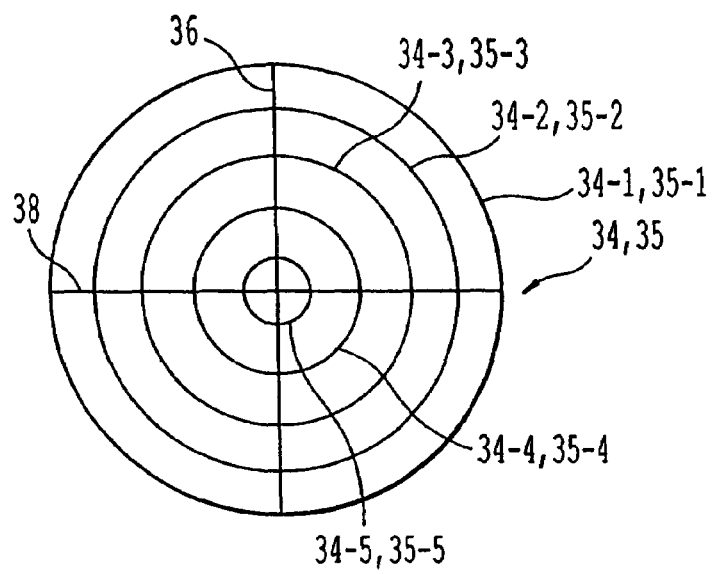
FIG. 22 is a top view of the multi-layer blank shown in FIG. 20 divided into four sections.
Figure 23:
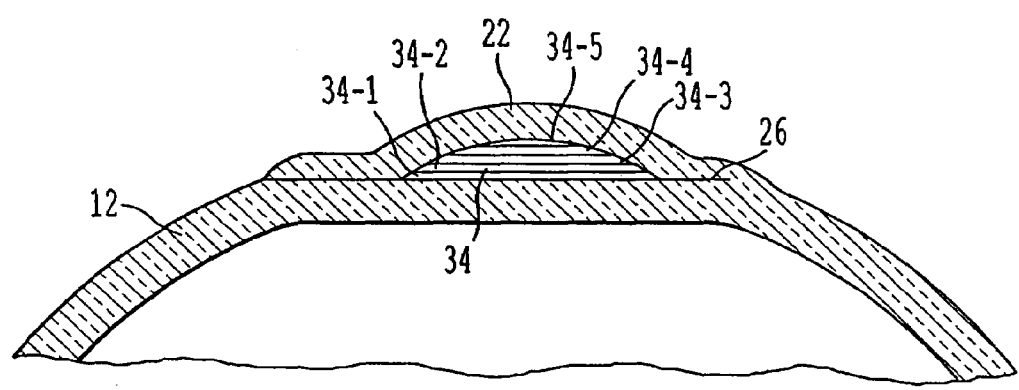
FIG. 23 is a side elevational view in section taken through the center of the eye showing the cornea and the flap-like portion reattached over the exposed surface of the cornea and a blank as shown in FIG. 19A being implanted therein.
Figure 24:
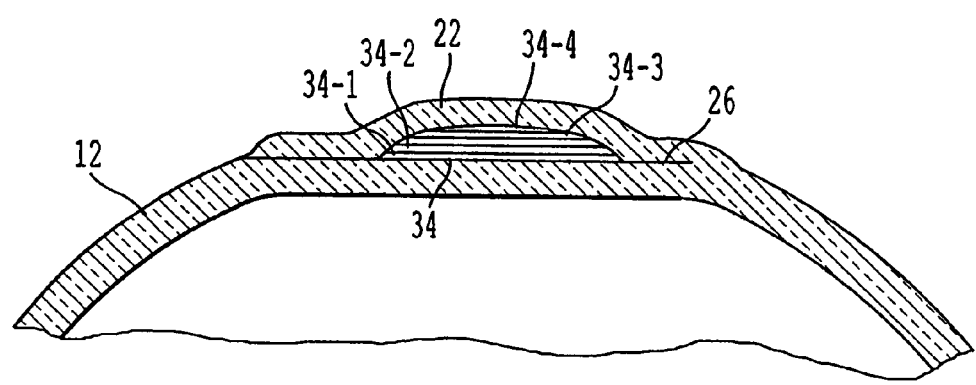
FIG. 24 is a side elevational view in section taken through the center of the eye showing the cornea and the flap-like portion reattached over the exposed surface of the cornea and a blank as shown in FIG. 19A being implanted therein, with one of the sections of the blank being removed.

It is further noted that the blank 18 can be configured as a multi-layer blank 34 as shown, for example in FIGS. 19A, 19B and 20. The multi-layer blanks 34 or 35 include, for example, sections 34-1 through 34-5, and sections 35-1 through 35-5, respectively, which can be separated from each other, as desired. The multi-layer blanks 34 and 35 each can include any number of layers having any suitable diameter, thickness and shape. Accordingly, the multi-layer blanks 34 or 35 can be implanted underneath a layer 22 in the cornea 12 in a manner similar to that discussed above with regard to blank 18. FIG. 23 illustrates an example of blank 34 implanted underneath a layer 22 of the cornea 12. When the layer 22 has been replaced and allowed to heal, the vision of the patient's eye can then be checked. If it is necessary to further adjust the curvature of the layer 22 to more accurately correct the vision disorder, one or more of the sections of the multi-layer blank 34 can be removed, as desired, to modify the corneal curvature as shown in FIG. 24. This removal of the appropriate sections can be performed by placing a small incision in the cornea 12 and removing the appropriate layer of the multi-layer blank 34. A similar process can be performed when blank 35 is implanted.

Alternatively, the layer 22 can be reseparated from the remainder form the cornea 12 so that appropriate layer of the multi-layer blank 34 can be removed. The layer 22 can then be replaced back over the remaining layers of the multi-layer blank 34 and permitted to heal. Also, the blanks 34 or 35 can be ablated, if desired, when the layer 22 is lifted to expose the blank 34 or 35. Furthermore, some or all of the layers 34-1 through 34-5, and 35-1 through 35-5 of the multi-layer blanks 34 and 35, respectively, may include the monomers or dyes as discussed above, so that those layers can be increased in volume or shrunk as desired, to further correct for the vision disorder without creating an incision in the cornea 12 or without reseparating the layer 22 from the cornea 12.

Figure 25:
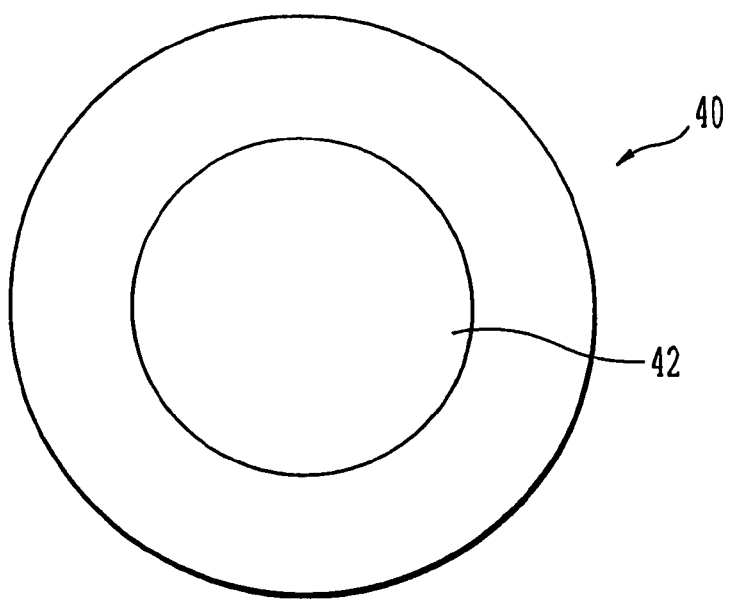
FIG. 25 is a top view of a ring-shaped blank according to another embodiment of the present invention.
Figure 26:
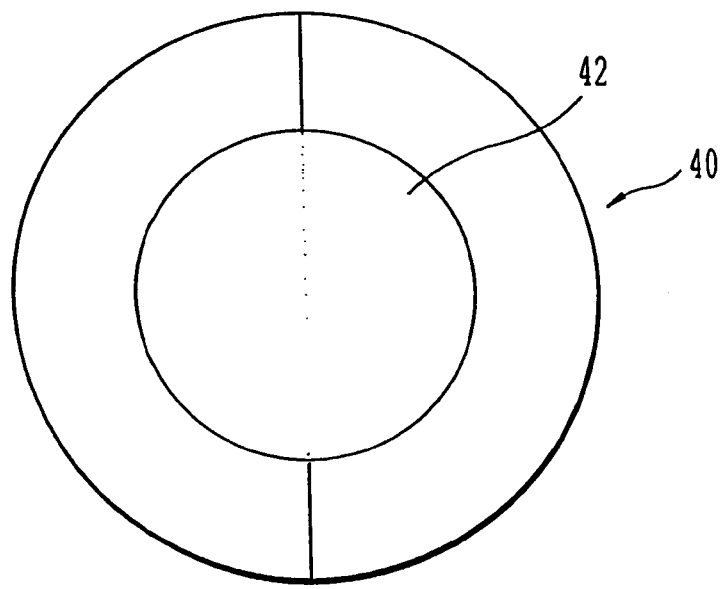
FIG. 26 is a top view of the ring-shaped blank shown in FIG. 23 divided into two sections.

As further shown in FIGS. 25 and 26, the multi-layer blanks 34 or 35 can be cut in half along line 36, in quarters along lines 36 and 38, or in any number of pieces, as desired. In this event, each of the layers 34-1 throughout 34-5, and 35-1 throughout 35-5, is either cut in half or quartered. Accordingly, the appropriate pieces of those layers 34-1 through 34-5, and 35-1 through 35-5, can be removed, as desired, to modify the curvature of the layer 22, as appropriate. Further portions of the layers 34-1 through 34-5, and 35-1 through 35-5, can be removed, as necessary, in the manners described above by reopening the layer 22 or through a small incision in the cornea 12, or alternatively, can be increased in volume or shrunk in the manners described above. Also, if desired, additional layers of the blanks 34 or 35 which were not initially implanted in the cornea 12 can be implanted through a small incision to change the curvature of the cornea 12.

In addition, as shown in FIG. 25, the blank can be a ring-shaped blank 40 having an opening 42 therein. The opening 42 can have any diameter ranging from a small hole to a diameter close to the outer diameter of the blank 40. As further shown in FIG. 26, the ring-shaped blank 40 can be separated, for example, into two halves 42-1 and 42-1, or in any number of pieces, as desired.

Figure 27:
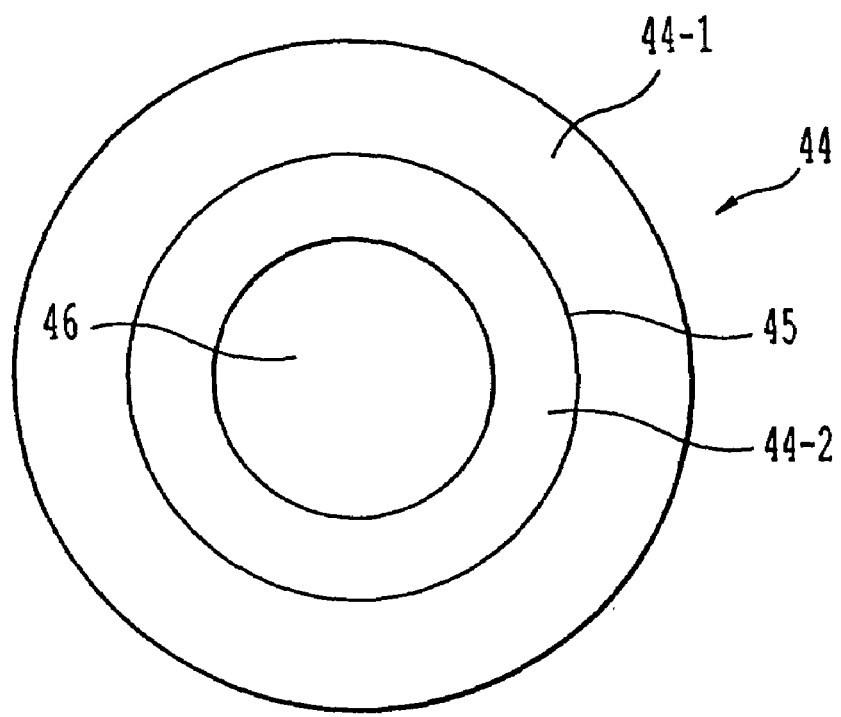
FIG. 27 is a top view of a multi-layer ring-shaped blank according to a further embodiment of the present invention.
Figure 28:
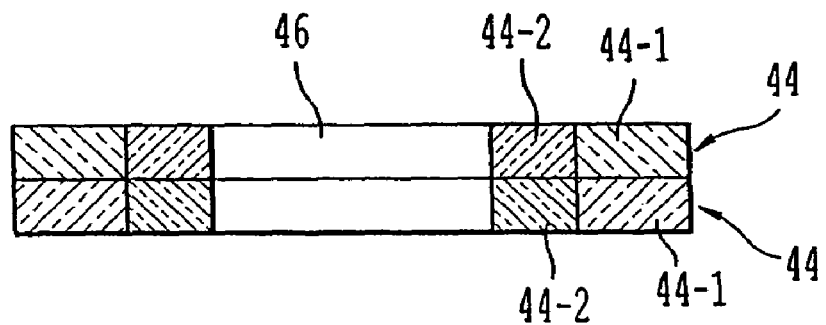
FIG. 28 is a cross-sectional view of the multi-layer ring-shaped blank shown in FIG. 27.
Figure 29:
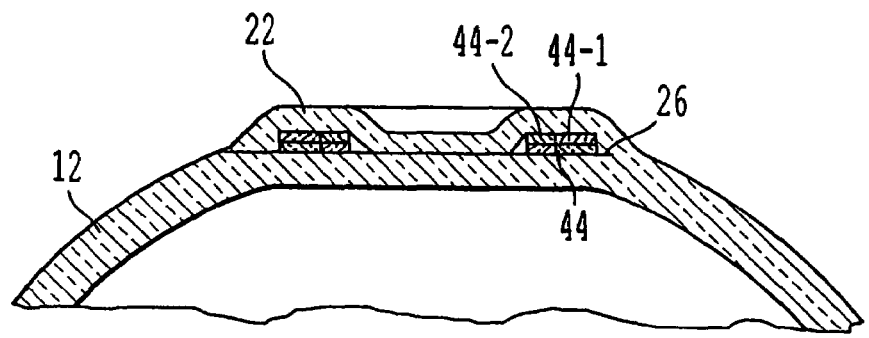
FIG. 29 is a side elevational view in section taken through the center of the eye showing the cornea and the flap-like portion reattached over the exposed surface of the cornea and a blank as shown in FIG. 28 being implanted therein.
Figure 30:
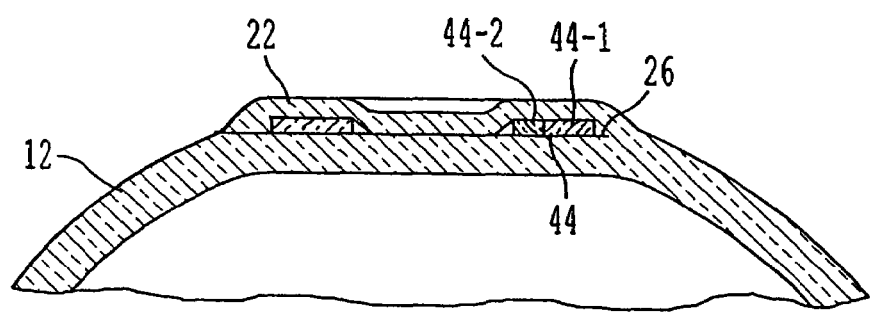
FIG. 30 is a side elevational view in section taken through the center of the eye showing the cornea and the flap-like portion reattached over the exposed surface of the cornea and a blank as shown in FIG. 28 being implanted therein, with one of the sections of the blank being removed.

Also, any of these types of ring-shaped blanks can be a multi-sectioned blank 44, as shown in FIGS. 27 and 28, having sections 44-1 and 44-2 and an opening 46 therein. As shown, section 44-2 fits inside the opening 45 of section 44-1 The multi-sectioned blanks 44 can also be stacked on top of each other to form a multi-layer blank 47 as shown in FIG. 28 specifically. As shown in FIG. 29, the multi-layer blank 47 can be implanted under the flap 22 in the cornea 12 to correct for high myopia. However, if the correction factor is too great, one of the layers 44, or one of the sections 44-1 or 44-2 of one of the layers 44, can be removed through a small incision in the cornea 12, so that only one section (e.g., section 44-2) of one layer 44 of the multi-layer blank remains under the flap 22, as shown in FIG. 30. This single section 44-2 can be used to correct for low myopia vision disorders. Also, as with blanks 34 and 35, further sections or layers 44 can be implanted in the cornea through a small incision to change the shape of the cornea as desired.

Figure 31:
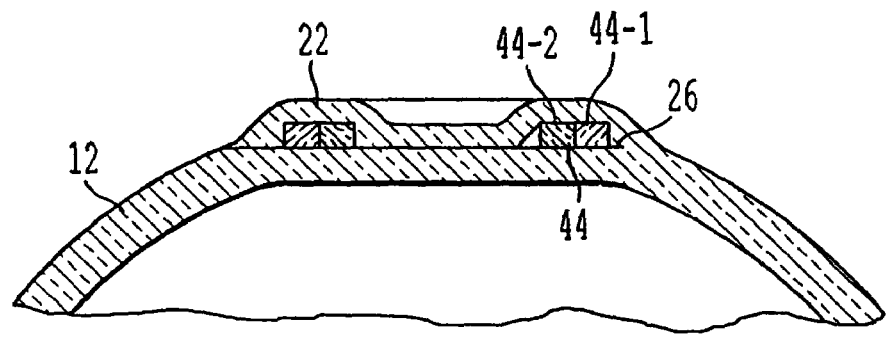
FIG. 31 is a side elevational view in section taken through the center of the eye showing the cornea and the flap-like portion reattached over the exposed surface of the cornea and one layer of the multi-layer blank as shown in FIG. 28 being implanted therein.
Figure 32:
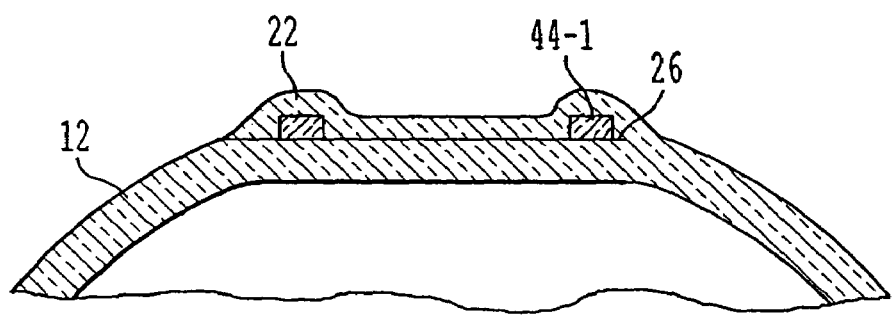
FIG. 32 is a side elevational view in section taken through the center of the eye showing the cornea and the flap-like portion reattached over the exposed surface of the cornea and one layer of the multi-layer blank as shown in FIG. 28 being implanted therein, with one of the sections of the blank being removed.

Also, as shown in FIG. 31, an entire single layer 44 having sections 44-1 and 44-2 can be implanted under the flap 22 in the cornea 12 to correct for a high myopia vision disorder. However, if it is determined that the correction factor is too great, one of the sections (e.g., section 44-2) can be removed from the cornea 12 through a small incision. In this event, the curvature of the flap 22 becomes less concave and thus, a lower correction power is achieved.

Figure 33:
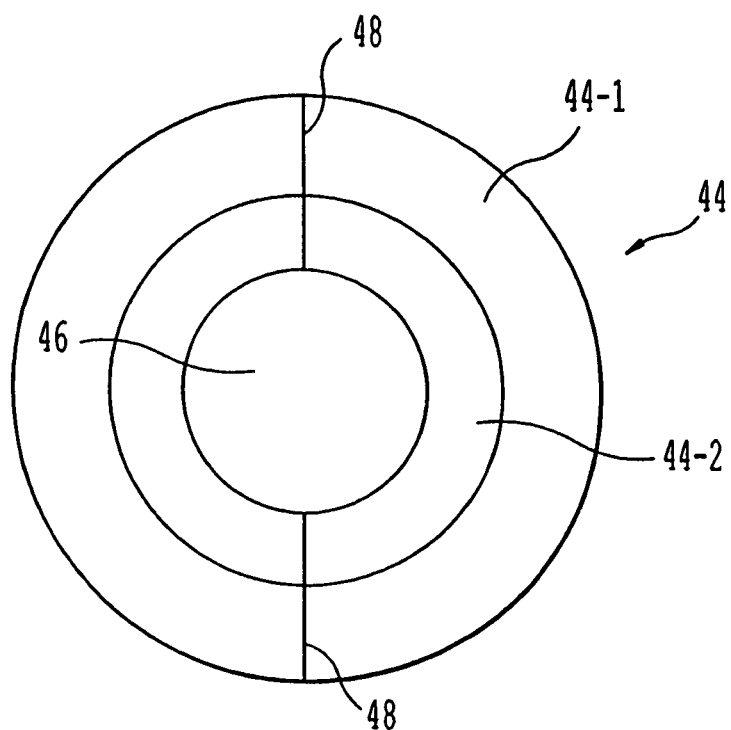
FIG. 33 is a top view of the multi-layer ring-shaped blank shown in FIG. 25 divided into two sections.
Figure 34:
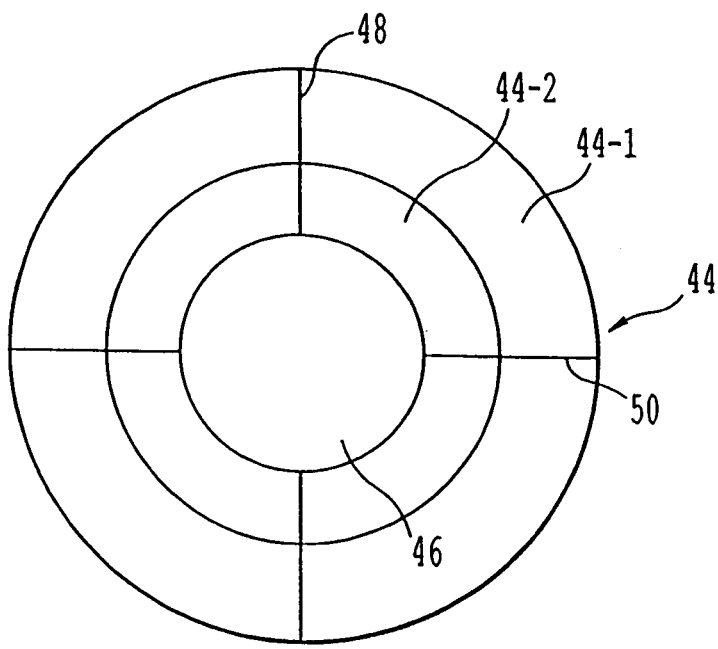
FIG. 34 is a top view of the multi-layer ring-shaped blank shown in FIG. 25 divided into four sections.

As shown in FIGS. 33 and 34, multi-layer blanks 44 can also be divided into sections along lines 48 and 50. Also, any of these ring-shaped blanks 40 and 44 may include the monomers and dyes as discussed above so that the volume of the blanks 40 and 44 can be increased or shrunk, as appropriate, to change their respective thickness, and to also change the diameter of the openings 42 and 46 therein, to change the curvature of the layer 22 to correct for the vision disorder, as appropriate. Also, these types of blanks 40 and 44 may include the monomers or dyes as discussed above to create the increase or shrinkage in volume as desired to modify the curvature of the layer 22 as appropriate to correct for the vision disorder.

It is further noted that any of the blanks discussed above need not be positioned at the center of the eye 10 along the optical axis of the eye. Rather, the blanks can be positioned anywhere in the cornea 12, as deemed appropriate, to change the shape of the cornea 12 as necessary to correct the vision disorder. Furthermore, the flap-like layer 22 need not be at the center of the cornea 12, but rather, can be in any portion of the cornea 12 and can have any suitable shape, such as annular about the cornea 12 and so on.

Embodiments of FIGS. 35–43

As seen in FIGS. 35–43, another embodiment of the present invention includes ablating the implant or blank 100 while the implant is positioned on the external surface 112 of the cornea 12, and then inserting the implant or blank 100 between layers of the cornea to correct myopia, hyperopia or an astigmatism.

Specifically, as shown in FIG. 35, an implant 100 is positioned on the surface of the cornea and the refractive error of the combination of the eye and the implant is measured using wavefront technology as is known in the art, after the cornea and conjunctiva has been rinsed and cleaned. Preferably, the implant is transparent or formed from an optically clear material and has about the same refractive index as the cornea. However, the implant can have any predetermined refractive properties desired and can thus act as a lens, or can have no refractive properties (i.e., a refractive index of zero).

As shown in FIGS. 36a–36d, implant 100 has a first side or surface 102, a second side or surface 104 and a portion 106 between the first and second sides. Sides 102 and 104 each can be concave (implant 100), convex (implant 100c), flat (implant 100b) or toric (implant 100d) or any combination thereof, and each side can be one shape while the other side is another shape, depending on the specific correction desired. For example, the first side 102 can be toric while the second side can be concave. Preferably, the implant is formed from a material that is pliable, and which would allow it to conform to the surface of the cornea. For example, the implant is preferably formed from the same materials as the blanks described above.

Using information or data supplied from wavefront technology, laser 108 is aimed at the implant and activated or fired (preferably at the first side 102), thereby ablating a portion of the implant 100 to correct the refractive error in the eye, as shown in FIG. 37. However, the laser can ablate any portion of the implant including portions 104 and 106. Preferably, the laser 108 is an excimer laser, but the laser can be any type of laser or any other device suitable for removing a portion of the implant to correct vision error. By ablating the implant in this manner, the implant is a custom implant for a particular eye of a patient and corrects the vision, in the eye to about 20/20 vision or better. To ensure proper vision, the eye can be remeasured using wavefront technology. If the vision of the eye in combination with the implant is not acceptable, the implant can be reablated or the process can be repeated with a new implant.

Additionally, the information used to ablate the implant while the implant is positioned on the surface of the cornea can be stored in a computer (not shown) that is coupled to the excimer laser. This information can then be used to perfectly ablate a second implant that is positioned under a flap. By forming a second implant in this manner, the ablated implant does not touch the exposed portion of the cornea under the flap and therefore no monomers that are formed during the ablation process are deposited on this surface. Monomers can be potential irritants to the cornea, which may cause problems in the eye.

The implant is removed from the surface of the cornea, and the implant and eye are properly rinsed to remove any mybomian gland secretion or any other undesirable material from the surface of the cornea and/or the implant. By rinsing the implant and eye, monomers that are formed during the ablation process are removed and will not stick to the stroma. Monomers could be potential irritants to the eye.

Figure 38:
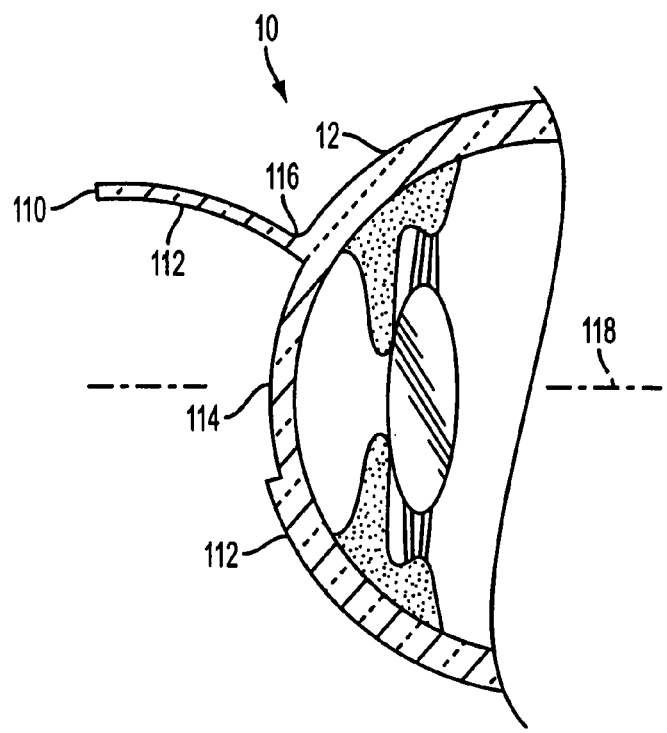
FIG. 38 is an elevational side view in section of the eye shown in FIG. 36 with a flap formed in the surface thereof.

If the correction in the combination of the eye and the implant is satisfactory, a flap 110 can be formed in the surface of the cornea, as seen in FIG. 38. The flap can be formed using a microkerotome, or any other knife or any other cutting device such as a short pulse or ultrashort pulse laser. The cornea is separated into a first corneal surface 112 and a second corneal surface 114. The first corneal surface faces in a posterior direction and the second corneal surface faces in an anterior section. The flap is completely separated from the cornea, except for a small hinge or portion 116. Hinge 116 allows the flap to be moved or pivoted to expose second surface 114, at least past or at the main optical axis 118 of the eye. In other words, the flap is pivoted about the hinge 116 to expose a large portion of the surface 114, including a portion of surface 114 that intersects the main optic axis of the eye. It is noted that it is not necessary to form the flap in this specific manner, and the flap may be completely removed from the cornea, or a pocket may be formed within the cornea.

When forming a pocket, the first and second corneal surfaces would not be attached at the main optical axis 118 or in a predetermined radius from the main optical axis. However, the first and second corneal surfaces would be attached at respective peripheries, except at an open portion, which would allow access thereinto. In other words, the cornea is separated into two surfaces, beneath the external surface. An opening is formed that connects the separated portion of the cornea to the external surface, so that a pocket is formed under the surface of the cornea, with access thereto via the opening. The pocket can extend substantially parallel or substantially perpendicular to the surface of the cornea, or any other direction desired.

Figure 39:
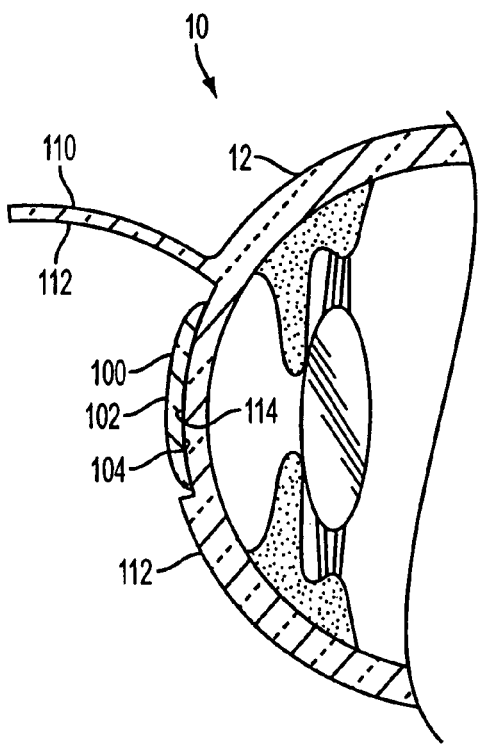
FIG. 39 is an elevational side view in section shown in the implant of FIG. 36 positioned on the surface of the exposed portion of the cornea.

As shown in FIG. 39, implant 100 is preferably placed or positioned adjacent or onto surface 114 of the cornea, but can be placed or positioned adjacent or on surface 112. For proper positioning, the implant can be marked for both rotational purposes and centering purposes. More precisely, the implant can have visual markings thereon that would allow for angular alignment (in the case of astigmatic correction) and/or a mark or markings that would allow for positioning the implant relative to the main optical axis. For a more complete discussion of markings for this purpose, refer to U.S. patent application Ser. No. 09/986,775, filed Nov. 9, 2001 and titled "Method and Apparatus for Alignment of Intracornal Inlay", the entire contents of which are herein incorporated by reference.

Figure 40:
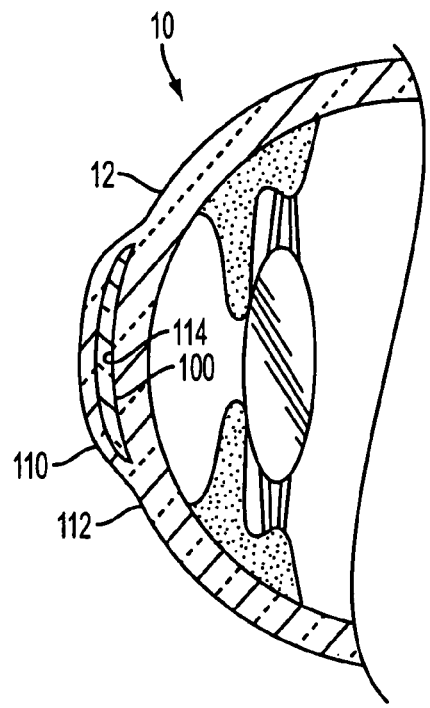
FIG. 40 is an elevational side view in section of the eye shown in FIG. 38 with the flap repositioned over the implant and the exposed portion of the cornea.

As shown in FIG. 40, flap 110 is repositioned over the first surface 102 of implant 100 and the second corneal surface 114, preferably without imposing any tension, or substantially no tension, thereon and without the use of any suturing devices or other methods of affixing the flap to the cornea. By not imposing any tension (or substantially no tension) on the flap, the refractive properties of the flap are maintained in the natural state. The vision through the cornea and into the eye will now be substantially the same as when the implant was positioned externally on the eye, which will be about 20/20 vision or better.

Additionally, it is not necessary to ablate the implant prior to implantation between the surfaces of the cornea. For example, it may be determined that the change in the shape of the cornea due to implantation of the implant between the layers of the cornea is sufficient to alter the vision of the eye. Furthermore, the implant can have refractive properties that are different than the refractive properties of the cornea, as stated above, which would properly alter the vision in the eye. The benefits of this type of implant are that the implant can be prefabricated to certain refractive indexes, reducing time by possibly eliminating or reducing the ablation procedure prior to implantation.

Figure 41:
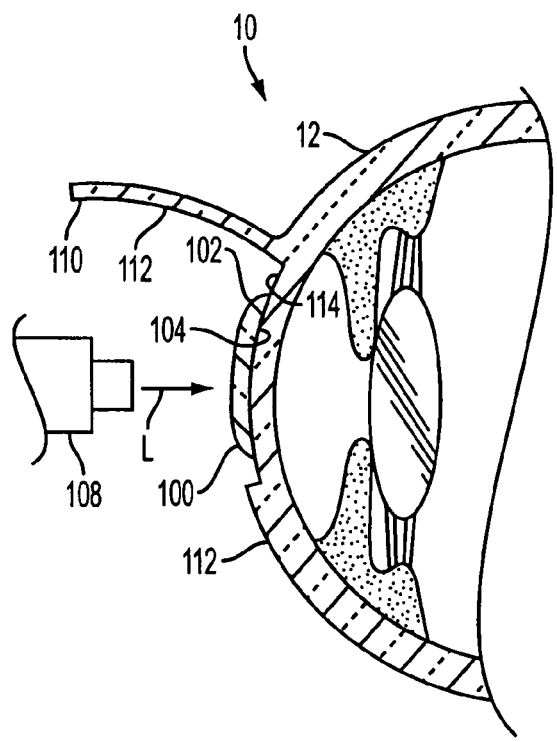
FIG. 41 is an elevational side view in section of the eye shown in FIG. 40 with a flap reformed in the surface of the cornea and the implant being further ablated by a laser.
Figure 42:
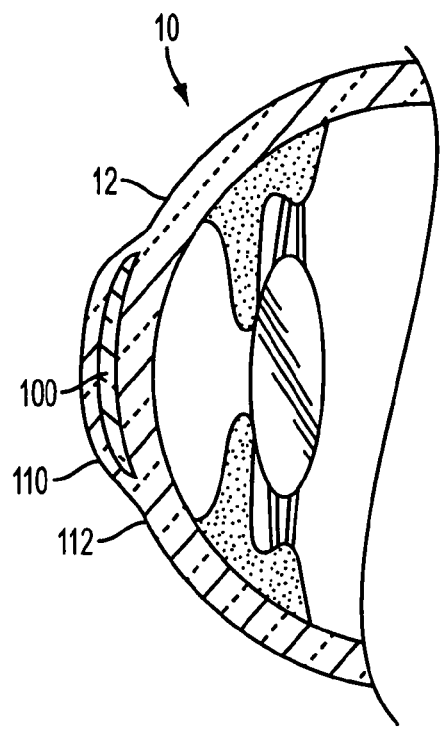
FIG. 42 is an elevational side view in section of the eye shown in FIG. 40 with the flap repositioned over the implant and the exposed portion of the cornea.
Figure 43:
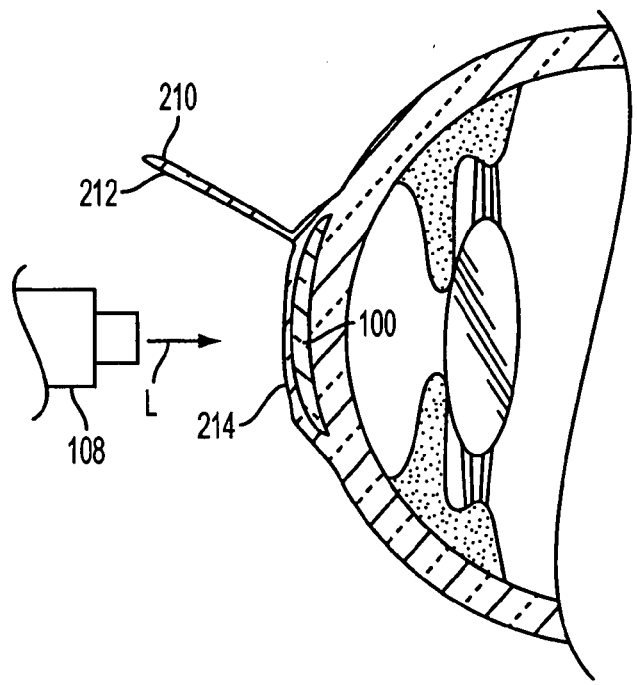
FIG. 43 is an elevational side view in section of the eye shown in FIG. 40 with another flap formed in the surface of the cornea and the cornea being ablated using a laser.

The flap is allowed to heal and reattach to the cornea, then the vision in the eye is remeasured to ensure proper vision. If it determined that the vision of the eye is not appropriate or suitable, the flap can be reformed or a new flap can be formed, which would allow access to the implant, as seen in FIG. 41. It is noted that the flap can be reformed at any time (i.e., a day, a month, a year, or any later time desired), and it is not necessary that the flap heal completely or even partially before it is reformed or moved to expose the implant 100 or a surface of the cornea. The implant can be reablated or repositioned, depending on the correction required, or a new implant can be positioned in place of the old implant and the procedure performed again. Furthermore, a second implant can be attached to the implant 100, which would also correct the vision in the eye, as discussed above. The flap is then repositioned (FIG. 42) again after the proper corrective procedures are preformed and allowed to heal as described above. This procedure may be preformed as often as needed or desired to obtain acceptable or near perfect vision.

Additionally, another flap 210 similar to flap 110, can be formed in the surface of the cornea and a portion of the cornea can be ablated in a similar manner as with the Lasik procedure. Flap 210 is formed by separating the cornea into a third surface 214 and a fourth surface 212, the third surface facing in an anterior direction and the fourth surface facing in a posterior direction. Preferably, laser 108 ablates surface 214 in the manner described above; however, surface 212 can be ablated, if desired. For a detailed description of one type of this procedure refer to U.S. patent application Ser. No. 09/843,141, filed Apr. 27, 2001 and titled "Adjustable Ablatable Inlay", and for a detailed description of the Lasik procedure, see U.S. Pat. No. 4,840,175, to Peyman, referenced above, the entire contents of both of which are herein incorporated by reference.

Furthermore, if desired, the implant 100 can be removed and the underlying surface 114 of the cornea can be ablated or the exposed surface 112 of the flap can be ablated. The combination of the ablation of a surface of the cornea and the shape and/or refractive index of the implant should be sufficient to provide the eye of the patient with near perfect or perfect vision. In other words, after the performance of any one or any combination of the above-described procedures, the eye should have 20/20 vision or better.

It is noted that the steps of this procedure do not necessarily need to be performed in the above-described order and can be performed in any order desired. For example, the flap can be performed prior to any step including positioning the implant on the surface of the cornea and ablating. By forming the flap first, any refractive properties that are changed due to the formation of the flap are known and accounted for when forming the implant. Also, if desired, the flap can sit for any desired length of time (i.e., one minute, one day, one month, or any other shorter or longer period of time) prior to positioning the implant on the surface and ablating. The flap is generally reformed relatively easily and, by waiting for this period of time, the refractive properties of the cornea with a flap are more readily known. Hence, these refractive properties can be taken into account when modifying the shape of the implant so as to achieve an even more accurate level of vision correction.

Embodiments of FIGS. 44–56

As seen in FIGS. 44–49, another embodiment of the present invention includes fixing a first or back portion 322 of implant or inlay 320 while the inlay is positioned on a surface 326 of the cornea 12 of eye 10. The inlay is then exposed to energy or irradiated at a front or second portion 324 of the inlay or blank 320 to correct myopia, hyperopia or an astigmatism.

Initially, as described above, wavefront technology is used to determine the proper correction for the refractive error in the eye. This can be done without an inlay positioned on the eye, with a inlay positioned on the exterior surface of the cornea 14, with an inlay 320 positioned on a surface 326 that is exposed by a flap 318, or at any other time or in any manner desired.

Figure 57:
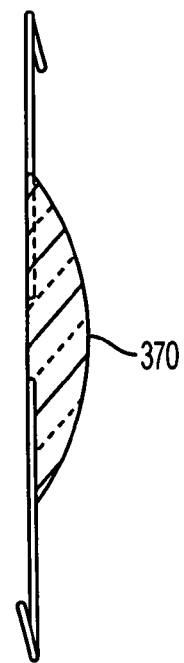
FIG. 57 is a side elevational view in section of an intraocular lens according to a fourth embodiment of the present invention.

Furthermore, it is noted that this type of inlay is not only suitable for the positioning in the cornea of the eye, but can also be used as an intraocular lens 370 (IOL), as shown in FIG. 57, or a contact lens. When used as an IOL, the implant or inlay can be positioned in addition to or in place of the natural lens of the eye (for example, the IOL can be fixed to the interior or the exterior of the natural lens). When used as a contact lens, the inlay is merely placed on the exterior surface of the cornea and can be removed and replaced at will.

The cornea is then separated into a first surface 328 and a second surface 326. First surface 328 faces in a posterior direction and second surface 326 faces in an anterior direction. Preferably, the cornea is separated in a manner that forms a substantially circular flap 318 that is connected to the cornea 12 by a hinge or small portion 330 at the periphery of the flap. However, the cornea can be separated into a pocket, a flap having a central portion attached at the main optical axis, a flap that is not attached to the cornea at all or in any other suitable manner.

Additionally, the flap 318 can be formed, so that a portion of the flap includes epithelial cells and stromal cells, as is generally done in a Lasik procedure, or the flap can be formed in only epithelial cells, as is generally done in the Lasek procedure. For example, a thin layer of epithelial cells can be completely removed or formed into a flap, as described herein, and the inlay then positioned under the epithelial cells. The epithelial cells are then put back in their original position to cover the inlay as described below.

Figure 44:
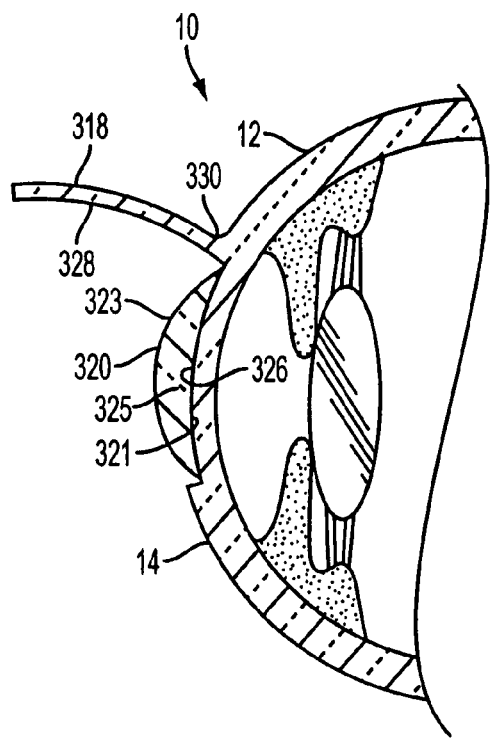
FIG. 44 is a side elevational view of the eye in section with an inlay according to a second embodiment of the present invention, placed adjacent a surface of the cornea that has been exposed by forming a flap in the surface of the cornea.

As shown in FIG. 44, inlay 320 is positioned adjacent or overlying surface 326; however, inlay 329 can be positioned adjacent or overlying surface 328 if desired. As noted above, wavefront technology can be used at this time to determine the precise correction required, if desired.

Inlay 320 has a first side or surface 321, a second side or surface 323 and a portion 325 between the first and second sides. Sides 321 and 323 each can be concave, convex, flat or toric, as described in the previous embodiments, or it any combination thereof, and each side can be one shape while the other side is another shape, depending on the specific correction desired. For example, the first side 321 can be toric while the second side 323 can be concave. Preferably, the inlay is formed from a material that is pliable, and which would allow it to conform to the surface of the cornea. For example, the inlay is preferably formed from the same materials as the blanks described above.

Additionally, the inlay can be formed of any number of materials that would allow the inlay to increase in volume or decrease in volume when exposed to an energy. For example, inlay 320 can include a silicone polymer which includes loose monomers that are responsive to light within a certain wavelength range, such as the short ultraviolet wavelength range or the blue light wavelength range. In response to the energy or light, the monomers become aggravated, and cross-linking occurs which increases the volume of the area of the inlay 320 being irradiated with the light.

The inlay can also include a polymer comprising a polycarbonate or acrylic material containing a dye or dyes manufactured, for example, by Centex Company. The dye or dyes absorb light within a certain wavelength range, such as the infrared wavelength range, which causes slight melting or softening of the material. This melting or softening results in a decrease or flattening of the irradiated area of the inlay, and thus reduces the volume of that area.

For further examples of the types of material suitable for changing the volume of a lens or inlay, see U.S Patent Application Publication No. US 2002/0016629 to Sandstedt et al., the entire contents of which are herein incorporated by reference.

Figure 45:
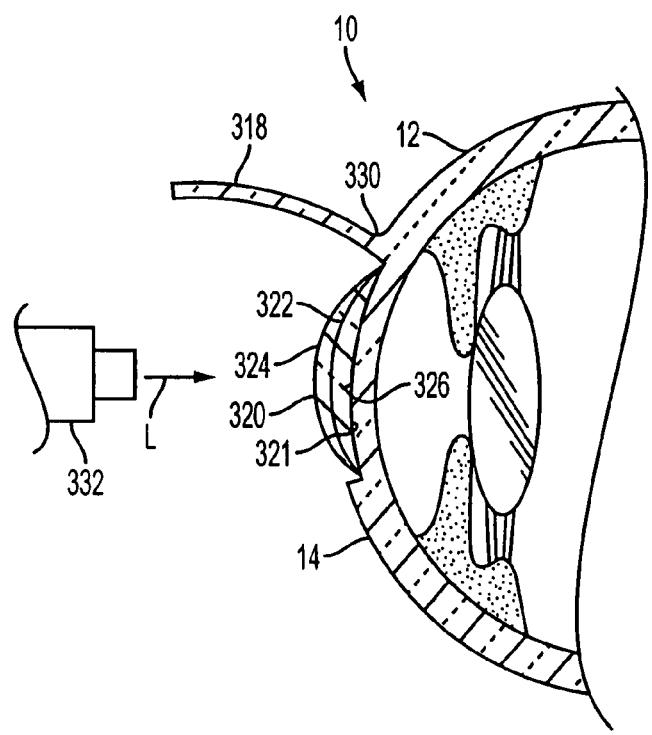
FIG. 45 is a side elevational view of the eye of FIG. 44, with a first portion of the inlay being exposed to laser light to fix the volume thereof.

As shown in FIG. 45, laser 332 is aimed and activated, firing a beam L in the direction of inlay 320. Laser 332 is programmed to contact portion 325 of inlay 320 adjacent second side 323. Preferably, this results in the polymerizing or fixing of only a back or first portion 322 of the inlay, and an unaffected front or second portion 324. Preferably, the back portion 322 is about half the volume of the portion 325. However, it is noted that the back portion can be any volume thereof, for example, the back portion can be almost the entire volume (i.e. about 99%) of portion 325 or it can be almost none of the volume (i.e. about 1%) of 325 or any percentage of the volume, desired.

Additionally, the inlay can be fixed or polymerized using any suitable energy, such as chemically or with thermal heat, or in any other manner desired.

It has been determined that although irradiating the entire inlay to increase or decrease the volume thereof, as described in the above described embodiments, is highly effective, the procedure can be further enhanced by having one portion (preferably the back portion) fixed, as described for this embodiment. Generally, in the above described methods, increasing or decreasing the size of the inlay can result in the back surface of the inlay changing shape, resulting in out-bulging or various changes on both the front and back surfaces of the inlay, making it difficult for the back surface to continually contact the cornea. This change in shape can result in an improper fit with the surface of the cornea (or the lens in the case of an IOL). Additionally, the back surface of the inlay contributes little to the refractive power of the inlay. Therefore, by fixing the volume of the back portion of the inlay, the shape of the back surface is fixed or maintained and will not change in shape due to the front portion being exposed to energy to change the shape thereof. Furthermore, the since the configuration of the back surface is fixed it will conform to the surface of the cornea, resulting in a more comfortable fit in the eye for a patient.

It is noted that this fixing of the inlay does not necessarily need to be performed while the inlay 320 is positioned adjacent the cornea. In many cases, it would be preferable to fix the first portion prior to positioning the inlay adjacent the cornea. For example, by fixing the first portion prior to positioning the inlay adjacent the cornea, the patient procedure can be performed at a faster rate. Additionally, since the back surface provides little in the way of refractive property, it may not necessary to change the volume of the first portion 322 to a specific refractive power, as long as the power is predeteremined.

Figure 46:
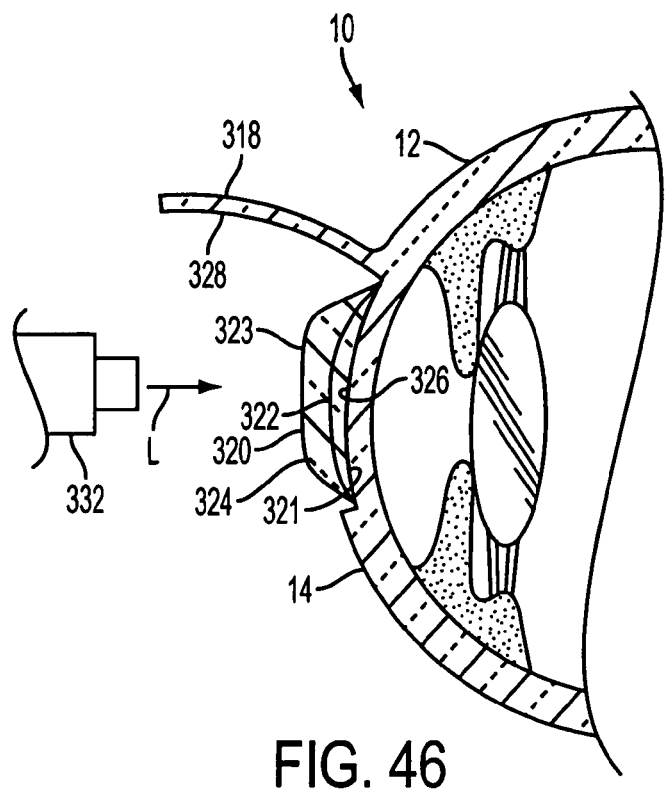
FIG. 46 is a side elevational view of the eye of FIG. 45, with a second portion of the inlay being exposed to laser light to increase the volume thereof.

Using laser the inlay 320 is then exposed to an energy or laser beam L. When the inlay includes material, such as a silicone polymer, the second portion 324 of the inlay increases in volume due to the cross-linking of the monomers or polymerization, as described above. When irradiated with light within a certain wavelength range (e.g., blue or ultraviolet light), become agitated and cross-link, which causes the second portion 324 of the inlay 320 to increase in size at the area of the irradiation, as shown in FIG. 46.

Figure 48:
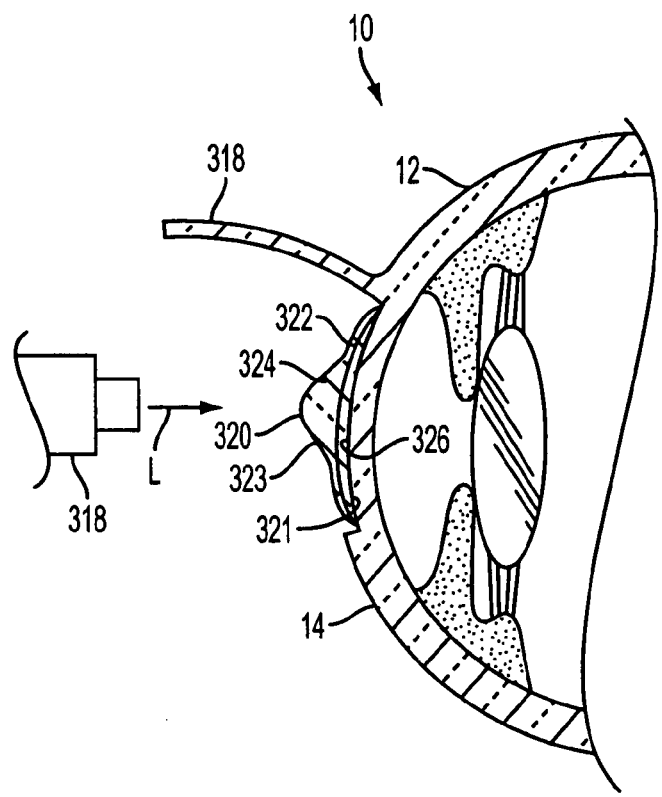
FIG. 48 is a side elevational view of the eye of FIG. 45, with a second portion of the inlay being exposed to laser light to decrease the volume thereof.

Furthermore, the inlay 320 can include a material comprising dyes as discussed above which will absorb energy or laser light (continuous or pulsed) of a particular wavelength (e.g., infrared light) that is irradiated onto an area of the second portion 324 of the inlay 320 to cause melting of the inlay 320 in that irradiated area, without ablating the irradiated area, as shown in FIG. 48. It is noted that when the pulsed laser light is focused properly to a location within the second portion 324 of the inlay 320, it can disrupt and thus shrink or melt the second portion 324 of the inlay without the need of an absorbent dye. An example of such a laser is a laser, which emits nano-second pulses, pico-second pulses or femto-second pulses of laser light. Furthermore, laser light having a wavelength that is absorbed by water, or other types of energy such as microwave radiation, radio frequency radiation, or thermal energy, can be used to cause shrinkage in the second portion 324 of the inlay without ablating the inlay 320 and without lifting the flap 318. In any of the above methods, the additional shaping of the inlay 320 is performed substantially without causing damage to the flap 318.

Additionally, the inlay can be exposed to energy using any suitable method, such as chemically or with thermal heat, or in any other manner desired.

Figure 47:
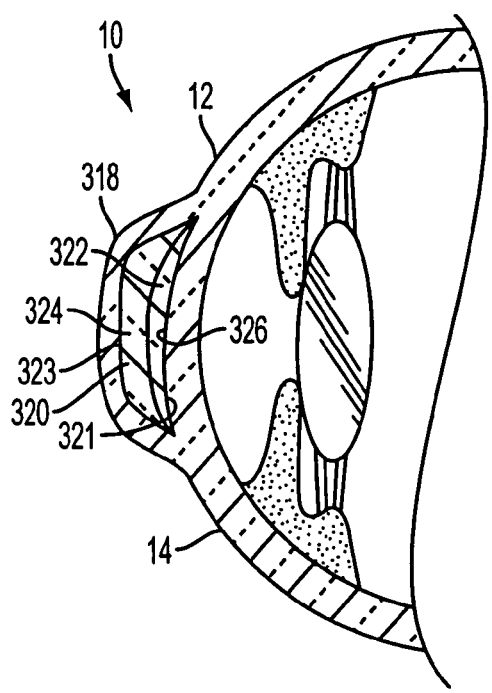
FIG. 47 is a side elevational view of the eye of FIG. 46 with the flap repositioned over the inlay.
Figure 49:
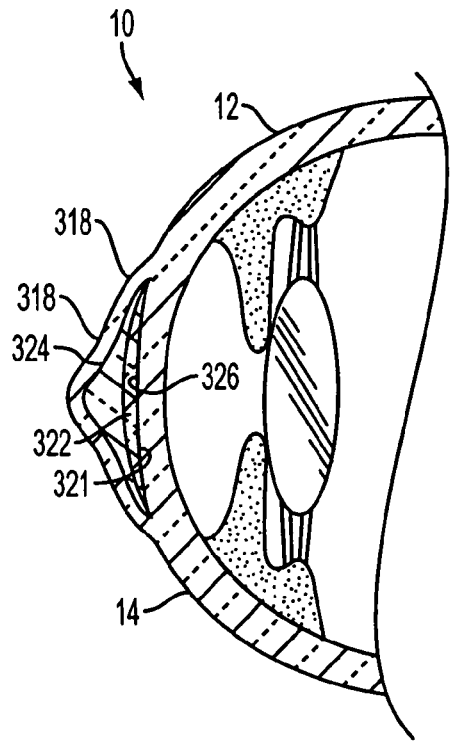
FIG. 49 is a side elevational view of the eye of FIG. 48 with the flap repositioned over the inlay.

As shown in FIGS. 47 and 49, the flap 318 is replaced over the inlay with increased or decreased volume, respectively. This change in curvature of the cornea causes a change in the refractive index of the cornea and therefore, corrects the refractive error in the eye.

Figure 50:
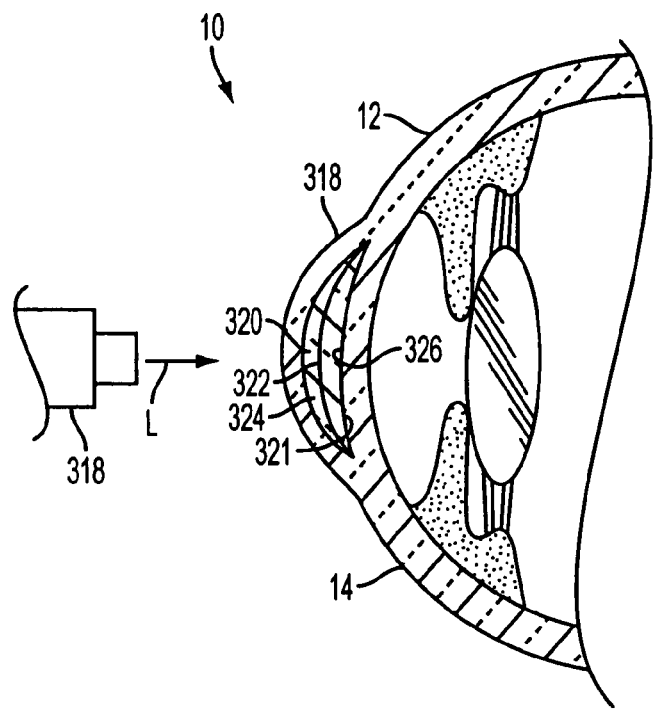
FIG. 50 is a side elevational view of the eye of FIG. 45 with the flap repositioned over the inlay, and the inlay being exposed to laser light to change the volume thereof.
Figure 51:
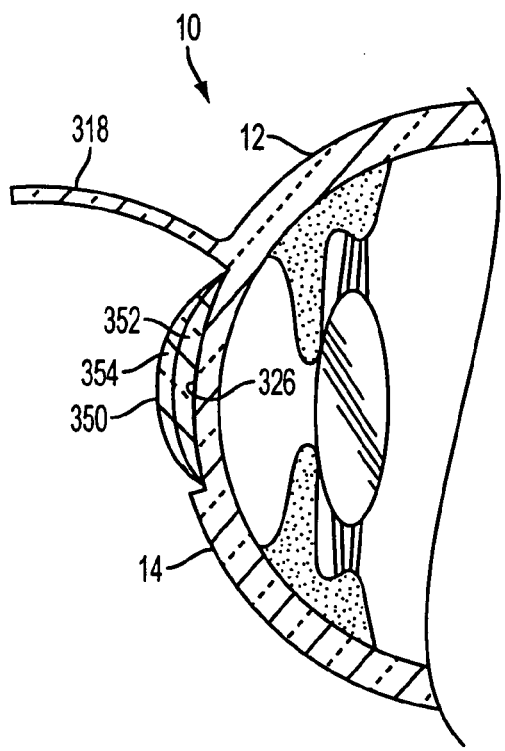
FIG. 51 is side elevational view of the eye in section with an inlay according to a third embodiment of the present invention, placed adjacent a surface of the cornea that has been exposed by forming a flap in the surface of the cornea.

As shown in FIG. 50, the volume of inlay 320 can be changed after the flap 318 is replaced over the inlay 320. In this particular instance, the laser is aimed and fired at the second portion 324 of the inlay 320, changing the volume of the inlay (i.e., increasing or decreasing the volume thereof) after the flap 318 has been positioned over the inlay. The result is substantially similar to the results shown in FIGS. 47 and 49, depending on whether the volume is increased or decreased.

As seen in FIGS. 51–55, another embodiment of the present invention includes forming first or back portion 352 of implant or inlay 350 with a fixed volume. A second or front portion 354 is then affixed to the back portion to form a inlay having a dual zones. The front or second portion 354 the inlay or blank 350 is then exposed to energy or irradiated to correct myopia, hyperopia or an astigmatism.

As with the embodiments described above for FIGS. 44–49, the inlay can be exposed to an energy or irradiated so that it increases or decreases in size. Additionally, the inlay can be exposed to energy using any suitable method, such as chemically or with thermal heat, or in any other manner desired.

First portion 352 can be formed of the materials described above for first portion 322, and the volume thereof can be fixed or polymerized prior to being affixed to second portion 354. However, first portion 352 can also be formed of any synthetic or organic material or combination thereof that is not affected when exposed to a predetermined energy, so that its volume remains substantially constant when the second surface or portion is exposed to a specific energy.

Figure 52:
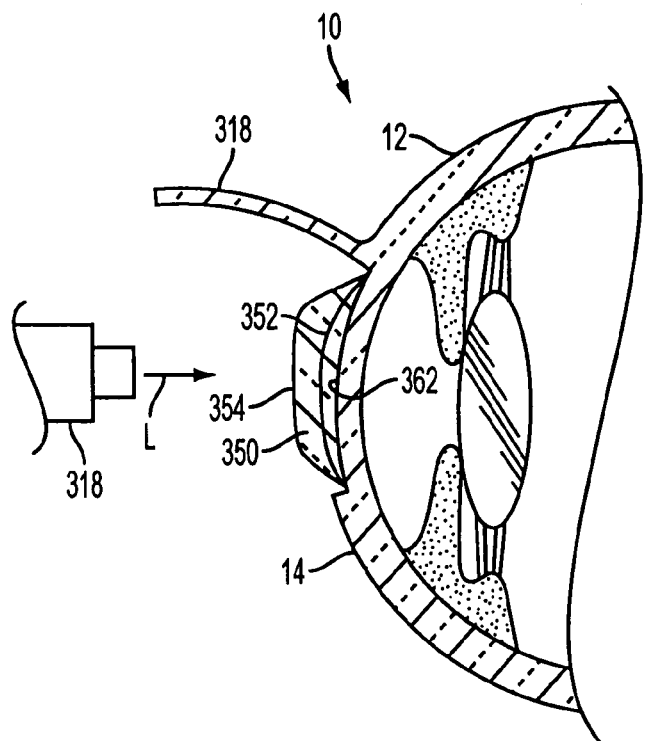
FIG. 52 is a side elevational view of the eye of FIG. 51, with a second portion of the inlay being exposed to laser light to increase the volume thereof, while the volume of the first portion remains substantially unchanged.
Figure 53:
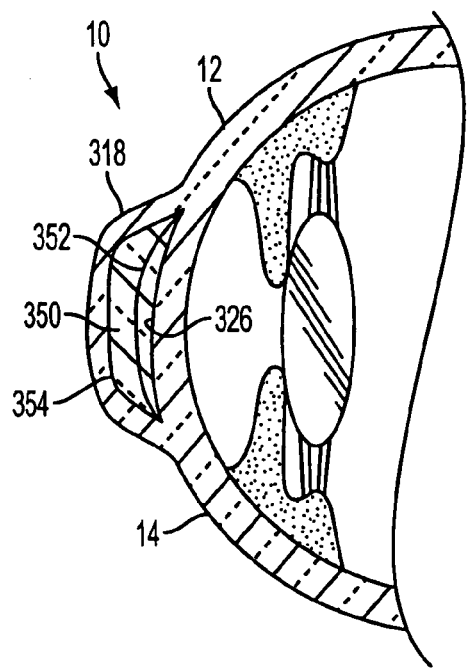
FIG. 53 is a side elevational view of the eye of FIG. 52 with the flap repositioned over the inlay.

Second portion 354 is formed from substantially the same material as described above for second portion 324. For example, second portion 354 can be formed from material including a silicone polymer, the second portion 324 of the inlay increases in volume due to the cross-linking of the monomers as described above. When exposed to energy or irradiated with light within a certain wavelength range (e.g., blue or ultraviolet light), become agitated and cross-link, which causes the second portion 354 of the inlay 320 to increase in size at the area of the irradiation, as shown in FIGS. 52 and 53.

Figure 54:
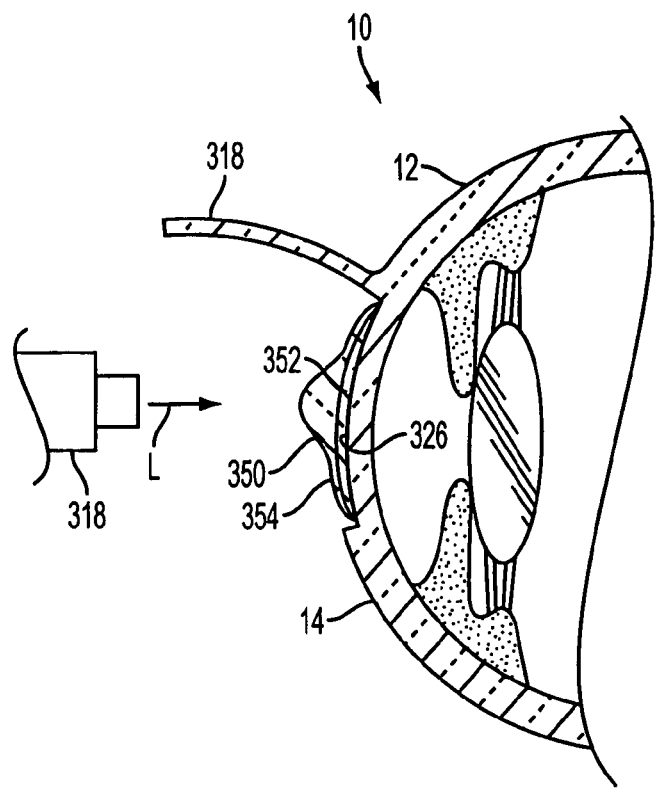
FIG. 54 is a side elevational view of the eye of FIG. 51, with a second portion of the inlay being exposed to laser light to decrease the volume thereof, while the volume of the first portion remains substantially unchanged.
Figure 55:
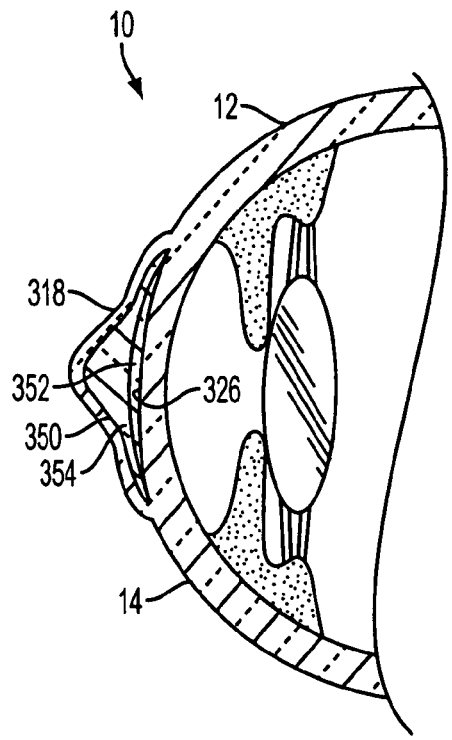
FIG. 55 is a side elevational view of the eye of FIG. 54 with the flap repositioned over the inlay.

Additionally, second portion 354 can include a material comprising dyes, as discussed above, which will absorb energy or laser light (continuous or pulsed) of a particular wavelength (e.g., infrared light) that is irradiated onto an area of the second portion 324 of the inlay 320 to cause melting of the inlay 320 in that irradiated area, without ablating the irradiated area, as shown in FIGS. 54 and 55.

Preferably, the second portion 354 is poured over first portion 352 and molded or solidified thereto or thereon, forming the bilayer inlay described above.

The embodiment described and shown in FIGS. 51–55 is similar to the embodiment shown in FIGS. 44–49 and any description thereof is applicable to this embodiment, other than any specific differences described herein.

Figure 56:
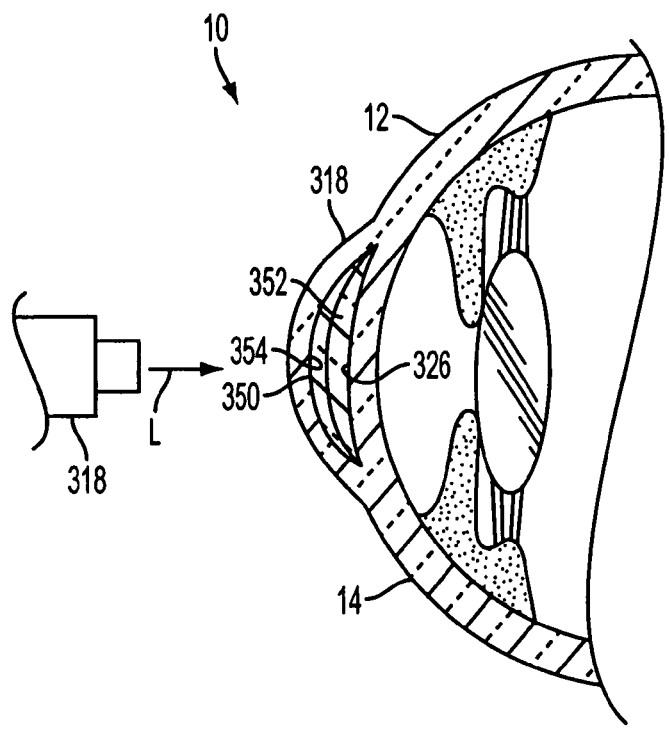
FIG. 56 is a side elevational view of the eye of FIG. 51 with the flap repositioned over the inlay, and the inlay being exposed to laser light to change the volume thereof.

As shown in FIG. 56, the volume of inlay 350 can be changed after the flap 318 is replaced over the inlay 350. In this particular instance, the laser is aimed and fired at the second portion 354 of the inlay 350, changing the volume of the inlay (i.e., increasing or decreasing the volume thereof) after the flap 318 has been positioned over the inlay. The result is substantially similar to the results shown in FIGS. 53 and 55, depending on whether in the volume is increased or decreased.

Furthermore, any inlay or blank described herein can be encapsulated in a thin layer of collagen, such as collagen type I, which would be tolerated by the tissue in the eye better than an inlay not encapsulated by collagen.

It is noted that each of this embodiments can be used to correct myopia, hyperopia and/or astigmatism, depending on which portions of the inlay are changed. For example, to correct astigmatism, it is possible to only alter a specific area (either increase or decreasing the volume thereof) to neutralize the general astigmatic area. Furthermore, each embodiment herein can be used in conjunction with the laser ablation procedure described above, if desired.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An inlay for correcting refractive error in an eye, comprising:
   a first portion having a first volume that remains substantially constant when exposed to an first energy; and
   a second unpolymerized portion having a second volume that is adapted to change when exposed to said energy;
   wherein said second volume is adapted to increase, when exposed to said energy, said energy being selected from the group consisting of laser light, a chemical and thermal heat.

2. An inlay for correcting refractive error in an eye, comprising:
   a first portion having a first volume that remains substantially constant when exposed to an first energy; and
   a second unpolymerized portion having a second volume that is adapted to change when exposed to said energy;
   a layer of collagen substantially covers said inlay.

3. A method of producing an inlay having a first portion and a second portion to correct the refractive error the eye, comprising the steps of
   forming an inlay having a first portion and a second portion,
   exposing the first portion to a first energy to polymerize and fix the volume thereof,
   positioning the inlay adjacent a surface of the cornea of the eye, and
   exposing the second portion to at least one of said first energy and a second energy to change the volume thereof.

4. A method according to claim 3, wherein
   the forming step includes forming the inlay from a material selected from the group consisting of synthetic material, organic material, and a combination of both synthetic and organic material.

5. A method according to claim 3, wherein
   the forming step includes forming the inlay so that the second portion overlies the first portion.

6. A method according to claim 3, wherein
   the forming step includes forming the inlay so that the first portion is positioned immediately adjacent an exposed surface of the cornea.

7. A method according to claim 6, wherein
   the forming step includes forming the inlay so that the second portion overlies said first portion.

8. A method according to claim 3, wherein
   the exposing the first portion to a first energy step includes exposing the first portion to laser light.

9. A method according to claim 3, wherein
   the exposing the second portion to change the volume thereof includes exposing the second portion formed from a polycarbonate or an acrylic material to said second energy to decrease the volume thereof.

10. A method according to claim 3, wherein
    the exposing the second portion to change the volume thereof includes exposing the second portion formed of silicone polymer to said second energy to increase the volume thereof.

11. An inlay for correcting refractive error in an eye, comprising:
    a polymerized first portion formed from a first material, at least a portion of said first portion positioned substantially adjacent a first surface of said inlay; and
    a second portion formed from an unpolymerized second material, at least a portion of said second portion positioned substantially adjacent a second surface of said inlay;
      wherein at least a portion of said second material is adapted to increase in volume, when exposed to energy selected from the group consisting of laser light, a chemical and thermal heat or decrease in volume, when exposed to a second energy, while the volume of said first material remains substantially unchanged.

12. An inlay according to claim 11, wherein
    said first material is selected from a group consisting of a polycarbonate, an acrylic material and a silicone polymer.

13. An inlay according to claim 11, wherein
    said second material is selected from a group consisting of a polycarbonate, an acrylic material and a silicone polymer.

14. An inlay according to claim 11, wherein
    said second portion overlies said first portion.

15. An inlay according to claim 11, wherein
    said first portion is adapted to be positioned immediately adjacent an exposed surface of the cornea.

16. An inlay according to claim 15, wherein
    said second portion is adapted to overlie said first portion.

17. An inlay according to claim 11, wherein
    said second volume is adapted to decrease, when exposed to energy selected from the group consisting of laser light, a chemical and thermal heat.

18. A method producing an inlay to correct the refractive error the eye, comprising the steps of
    forming a first portion of the inlay having a first material therein,
    fixing the volume of the first material,
    attaching a second portion of the inlay to the first portion, the second portion having an unpolymerized second material therein,
    positioning the inlay in the eye, and
    exposing the second material to energy to change the volume of the second portion.

19. A method according to claim 18, wherein
    the forming step includes forming the first portion of the inlay from a material selected from the group consisting of a polycarbonate, an acrylic material and a silicone polymer.

20. A method according to claim 18, wherein
    the attaching step includes attaching the second portion of the inlay to the first portion of the inlay so that the second portion overlies the first portion.

21. A method according to claim 18, wherein
    the forming step includes forming the first portion of the inlay so that the first portion is positioned immediately adjacent an exposed surface of the cornea.

22. A method according to claim 21, wherein
    the attaching step includes attaching the second portion of the inlay to the first portion of the inlay so that the second portion overlies said first portion.

23. A method according to claim 18, wherein
    the fixing the volume of the first material step includes exposing the first material to laser light.

24. A method according to claim 18, wherein
    the exposing the second material to change the volume thereof includes exposing the second material formed from a polycarbonate or an acrylic material to an energy to decrease the volume thereof.

25. A method according to claim 18, wherein
    the exposing the second material to change the volume thereof includes exposing the second material formed from a silicone polymer to an energy to increase the volume thereof.

26. An inlay for correcting refractive error in an eye, comprising:
    a first surface;
    a second surface opposite said first surface;
    a first portion having a first polymerized volume that remains substantially constant when exposed to an energy, said first polymerized volume being located adjacent said first surface of said inlay and extending to about the periphery of said first surface;
    a second portion having a second volume that is adapted to change when exposed to said energy; and a third portion having a third volume that is adapted to change, substantially without ablation, when exposed to said energy;

wherein said first and second portions are formed from the same material; and wherein said third volume is adapted to increase, when exposed to energy selected from the group consisting of laser light, a chemical and thermal heat.

27. An inlay according to claim 26, wherein said material is selected from the group consisting of a polycarbonate, an acrylic material and a silicone polymer.

28. An inlay according to claim 26, wherein said second portion overlies said first portion.

29. An inlay according to claim 26, wherein said first portion is adapted to be positioned immediately adjacent an exposed surface of the cornea.

30. An inlay according to claim 29, wherein said second portion is adapted to overlie said first portion.

31. An inlay according to claim 26, wherein said energy is laser light.

32. An inlay according to claim 26 wherein said third portion is formed from a material selected from a group consisting of synthetic material, organic material, and a combination of both synthetic and organic material.

33. An inlay according to claim 26, wherein said third volume is adapted to decrease, when exposed to energy selected from the group consisting of laser light, a chemical and thermal heat.

34. An inlay for correcting refractive error in an eye, comprising one of the following:

a first portion having a first volume that remains substantially constant when exposed to an energy, and a second portion having a second volume that is adapted to change when exposed to said energy; and a third portion having a third volume that is adapted to change, substantially without ablation, when exposed to said energy, wherein said third volume is adapted to increase, when exposed to energy selected from the group consisting of laser light, a chemical and thermal heat.

35. An inlay according to claim 1, wherein said inlay is a contact lens.

36. An inlay according to claim 35, wherein said contact lens is adapted to be positioned on the exterior surface of the cornea.

37. An inlay according to claim 36, wherein said second volume is adapted to increase or decrease when exposed to energy selected from the group consisting of laser light, a chemical, and thermal heat.

* * * * *